(12) United States Patent
Di Fabio et al.

(10) Patent No.: US 7,446,108 B2
(45) Date of Patent: Nov. 4, 2008

(54) TRI-AND TETRAAZA-ACENAPHTHYLEN DERIVATIVES AS CRF RECEPTOR ANTAGONISTS

(75) Inventors: Romano Di Fabio, Verona (IT); Gabriella Gentile, Verona (IT); Yves St Denis, Verona (IT)

(73) Assignees: Neurocrine, Inc., San Diego, CA (US); SmithKline Beecham (Cork) Ltd, Cork (IE)

( * ) Notice: Subject to any disclaimer, the term of this patent is extended or adjusted under 35 U.S.C. 154(b) by 434 days.

(21) Appl. No.: 10/477,886

(22) PCT Filed: May 21, 2002

(86) PCT No.: PCT/GB02/02377

§ 371 (c)(1), (2), (4) Date: May 28, 2004

(87) PCT Pub. No.: WO02/094826

PCT Pub. Date: Nov. 28, 2002

(65) Prior Publication Data

US 2004/0198726 A1    Oct. 7, 2004

Related U.S. Application Data

(60) Provisional application No. 60/292,660, filed on May 21, 2001.

(51) Int. Cl.
*A01N 43/54* (2006.01)
*C07D 239/00* (2006.01)

(52) U.S. Cl. .................. 514/267; 544/251

(58) Field of Classification Search ......... 544/251; 514/267

See application file for complete search history.

(56) References Cited

U.S. PATENT DOCUMENTS 6,514,982 B1 * 2/2003 Haddach et al. ........ 514/267

FOREIGN PATENT DOCUMENTS

| WO | WO 97/44038 | 11/1997 |
| WO | WO 98/08847 | 3/1998 |
| WO | WO 00/27846 | 5/2000 |
| WO | WO 03/008414 | 1/2003 |

OTHER PUBLICATIONS

Banker, Gilbert S. et al., Modem Pharmaceutics, Marcel Dekker, New York, 1996, pp. 451 and 596.*
Wolff, Manfred E., Burger's Medicinal Chemistry and Drug Discovery, Fifth Ed., vol. 1: Principles and Practice, John Wiley & Sons, 1995, pp. 975-977.*
Akimoto, et al., Chem. Abstracts, 1993, vol. 118, No. 21, XP002207951.
Akimoto et al. Chem. Abstracts, 118(21): 1993. XP002207951.

* cited by examiner

*Primary Examiner*—James O. Wilson
*Assistant Examiner*—Erich A Leeser
(74) *Attorney, Agent, or Firm*—Laura K. Madden; Loretta Sauermelch; Mary McCarthy

(57) ABSTRACT

CRF receptor antagonists are disclosed which have utility in the treatment of a variety of disorders, including the treatment of disorders manifesting hypersecretion of CRF in a warm-blooded animals, such as stroke. The CRF receptor antagonists of this invention have the following structure:

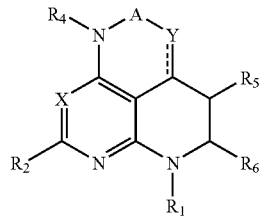

including stereoisomers, prodrugs and pharmaceutically acceptable salts thereof, $R_1$, $R_2$, $R_4$, $R_5$, $R_6$, A, X, and Y are as defined herein. Compositions containing a CRF receptor antagonist in combination with a pharmaceutically acceptable carrier are also disclosed, as well as methods for use of the same.

5 Claims, No Drawings

US 7,446,108 B2

TRI-AND TETRAAZA-ACENAPHTHYLEN DERIVATIVES AS CRF RECEPTOR ANTAGONISTS

CONTINUITY DATA

This application is a 371 of PCT/GB02/02377, filed on May 21, 2002 and which claims benefit of U.S. provisional application 60/292,660, filed on May 21, 2001.

TECHNICAL FIELD

This invention relates generally to CRF receptor antagonists, and to methods of treating disorders by administration of such antagonists to a warm-blooded animal in need thereof.

BACKGROUND OF THE INVENTION

The first corticotropin-releasing factor (CRF) was isolated from ovine hypothalami and identified as a 41-amino acid peptide (Vale et al., Science 213:1394-1397, 1981). Subsequently, sequences of human and rat CRF were isolated and determined to be identical, but different from ovine CRF in 7 of the 41 amino acid residues (Rivier et al., Proc. Natl. Acad. Sci. USA 80:4851, 1983; Shibahara et al., EMBO J. 2:775, 1983).

CRF has been found to produce profound alterations in endocrine, nervous and immune system function. CRF is believed to be the major physiological regulator of the basal and stress-release of adrenocorticotropic hormone ("ACTH"), β-endorphin, and other pro-opiomelanocortin ("POMC")-derived peptides from the anterior pituitary (Vale et al., Science 213:1394-1397, 1981). Briefly, CRF is believed to initiate its biological effects by binding to a plasma membrane receptor which has been found to be distributed throughout the brain (DeSouza et al., Science 224: 1449-1451, 1984), pituitary (DeSouza et al., Methods Enzymol. 124:560, 1986; Wynn et al., Biochem. Biophys. Res. Comm. 110:602-608, 1983), adrenals (Udelsman et al., Nature 319:147-150, 1986) and spleen (Webster, E. L., and E. S. DeSouza, Endocrinology 122:609-617, 1988) The CRF receptor is coupled to a GTP-binding protein (Perrin et al., Endocrinology 118:1171-1179, 1986) which mediates CRF-stimulated increase in intracellular production of cAMP (Bilezikjian, L. M., and W. W. Vale, Endocrinology 113:657-662, 1983). The receptor for CRF has now been cloned from rat (Perrin et al., Endo 133(6):3058-3061, 1993), and human brain (Chen et al., PNAS 90(19):8967-8971, 1993; Vita et al., FEBS 335(1):1-5, 1993). This receptor is a 415 amino acid protein comprising seven membrane spanning domains. A comparison of identity between rat and human sequences shows a high degree of homology (97%) at the amino acid level.

In addition to its role in stimulating the production of ACTH and POMC, CRF is also believed to coordinate many of the endocrine, autonomic, and behavioral responses to stress, and may be involved in the pathophysiology of affective disorders. Moreover, CRF is believed to be a key intermediary in communication between the immune, central nervous, endocrine and cardiovascular systems (Crofford et al., J. Clin. Invest. 90:2555-2564, 1992; Sapolsky et al., Science 238:522-524, 1987; Tilders et al., Regul. Peptides 5:77-84, 1982). Overall, CRF appears to be one of the pivotal central nervous system neurotransmitters and plays a crucial role in integrating the body's overall response to stress.

Administration of CRF directly to the brain elicits behavioral, physiological, and endocrine responses identical to those observed for an animal exposed to a stressful environment. For example, intracerebroventricular injection of CRF results in behavioral activation (Sutton et al., Nature 297:331, 1982), persistent activation of the electroencephalogram (Ehlers et al., Brain Res. 278:332, 1983), stimulation of the sympathoadrenomedullary pathway (Brown et al., Endocrinology 110:928, 1982), an increase of heart rate and blood pressure (Fisher et al., Endocrinology 110:2222, 1982), an increase in oxygen consumption (Brown et al., Life Sciences 30:207, 1982), alteration of gastrointestinal activity (Williams et al., Am. J. Physiol. 253:G582, 1987), suppression of food consumption (Levine et al., Neuropharmacology 22:337, 1983), modification of sexual behavior (Sirinathsinghji et al., Nature 305:232, 1983), and immune function compromise (Irwin et al., Am. J. Physiol. 255:R744, 1988).

Furthermore, clinical data suggests that CRF may be hypersecreted in the brain in depression, anxiety-related disorders, and anorexia nervosa. (DeSouza, Ann. Reports in Med. Chem. 25:215-223, 1990). Accordingly, clinical data suggests that CRF receptor antagonists may represent novel antidepressant and/or anxiolytic drugs that may be useful in the treatment of the neuropsychiatric disorders manifesting hypersecretion of CRF.

The first CRF receptor antagonists were peptides (see, e.g., Rivier et al., U.S. Pat. No. 4,605,642; Rivier et al., Science 224:889, 1984). While these peptides established that CRF receptor antagonists can attenuate the pharmacological responses to CRF, peptide CRF receptor antagonists suffer from the usual drawbacks of peptide therapeutics including lack of stability and limited oral activity. More recently, small molecule CRF receptor antagonists have been reported. For example, substituted 4-thio-5-oxo-3-pyrazoline derivatives (Abreu et al., U.S. Pat. No. 5,063,245) and substituted 2-aminothiazole derivatives (Courtemanche et al., Australian Patent No. AU-A-41399/93) have been reported as CRF receptor antagonists. These particular derivatives were found to be effective in inhibiting the binding of CRF to its receptor in the 1-10 µM range and 0.1-10 µM range, respectively.

Due to the physiological significance of CRF, the development of biologically-active small molecules having significant CRF receptor binding activity and which are capable of antagonizing the CRF receptor remains a desirable goal. Such CRF receptor antagonists would be useful in the treatment of endocrine, psychiatric and neurologic conditions or illnesses, including stress-related disorders in general.

While significant strides have been made toward achieving CRF regulation through administration of CRF receptor antagonists, there remains a need in the art for effective small molecule CRF receptor antagonists. There is also a need for pharmaceutical compositions containing such CRF receptor antagonists, as well as methods relating to the use thereof to treat, for example, stress-related disorders. The present invention fulfills these needs, and provides other related advantages.

SUMMARY OF THE INVENTION

In brief, this invention is generally directed to CRF receptor antagonists, and more specifically to CRF receptor antagonists having the following general structure (I):

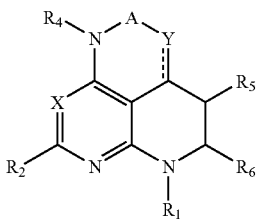

including stereoisomers, prodrugs and pharmaceutically acceptable salts thereof, wherein $R_1$, $R_2$, $R_4$, $R_5$, $R_6$, A, X, and Y are as defined below.

The CRF receptor antagonists of this invention have utility over a wide range of therapeutic applications, and may be used to treat a variety of disorders or illnesses, including stress-related disorders. Such methods include administering an effective amount of a CRF receptor antagonist of this invention, preferably in the form of a pharmaceutical composition, to an animal in need thereof Accordingly, in another embodiment, pharmaceutical compositions are disclosed containing one or more CRF receptor antagonists of this invention in combination with a pharmaceutically acceptable carrier and/or diluent.

These and other aspects of the invention will be apparent upon reference to the following detailed description. To this end, various references are set forth herein which describe in more detail certain procedures, compounds and/or compositions, and are hereby incorporated by reference in their entirety.

DETAILED DESCRIPTION OF THE INVENTION

The present invention is directed generally to compounds useful as corticotropin-releasing factor (CRF) receptor antagonists.

In a first embodiment, the CRF receptor antagonists of this invention have the following structure (I):

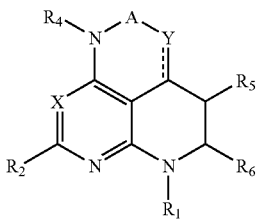

including stereoisomers, prodrugs and pharmaceutically acceptable salts thereof, wherein:

A is a bond or C=(Z);
X is nitrogen or $CR_3$;
Y is —N=, —N($R_7$)—, C($R_8$)= or —O—;
Z is O, S or $NR_9$;
$R_1$ is alkyl, substituted alkyl, aryl, substituted aryl, heteroaryl, or substituted heteroaryl;
$R_2$ is hydrogen, alkyl, substituted alkyl, alkoxy, thioalkyl, halo, cyano, haloalkyl;
$R_3$ is hydrogen, alkyl, substituted alkyl, halo or haloalkyl;
$R_4$ is hydrogen, alkyl, substituted alkyl, C(O)$R_1$, aryl, substituted aryl, heterocycle or substituted heterocycle;

$R_5$ is hydrogen, halogen, alkyl, substituted alkyl, aryl, substituted aryl, heteroaryl, substituted heteroaryl, alkoxy, thioalkyl, C(O)$R_1$, $NR_{10}R_{11}$ or cyano;
$R_6$ is hydrogen, halogen, alkyl, substituted alkyl, aryl, substituted aryl, heteroaryl, substituted heteroaryl, alkoxy, thioalkyl, C(O)$R_1$, $NR_{10}R_{11}$ or cyano;
$R_7$ is hydrogen, alkyl, substituted alkyl, C(O)$R_1$, aryl, substituted aryl, heteroaryl, or substituted heteroaryl;
$R_8$ is hydrogen, halogen, alkyl, substituted alkyl, aryl, substituted aryl, heteroaryl, substituted heteroaryl, alkoxy, thioalkyl, C(O)alkyl, $NR_{10}R_{11}$ or cyano;
$R_9$ is hydrogen, alkyl, substituted alkyl, aryl, substituted aryl, heteroaryl, or substituted heteroaryl; and
$R_{10}$, $R_{11}$ are the same or different and are independently hydrogen, alkyl, substituted alkyl, aryl, substituted aryl, heteroaryl, substituted heteroaryl.

As used herein, the above terms have the following meaning:

"Alkyl" means a straight chain or branched, noncyclic or cyclic, unsaturated or saturated aliphatic hydrocarbon containing from 1 to 10 carbon atoms, while the term "lower alkyl" has the same meaning as alkyl but contains from 1 to 6 carbon atoms. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, —CH$_2$cyclopropyl, —CH$_2$cyclobutyl, —CH$_2$cyclopentyl, —CH$_2$cyclohexyl, and the like; while unsaturated cyclic alkyls include cyclopentenyl and cyclohexenyl, and the like. Cyclic alkyls, also referred to as "homocyclic rings," and include di- and polyhomocyclic rings such as decalin and adamantyl, Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1 butynyl, and the like.

"Aryl" means an aromatic carbocyclic moiety such as phenyl or naphthyl.

"Arylalkyl" means an alkyl having at least one alkyl hydrogen atoms replaced with an aryl moiety, such as benzyl, —CH$_2$-(1 or 2-naphthyl), —(CH$_2$)$_2$phenyl, —(CH$_2$)$_3$phenyl, —CH(phenyl)$_2$, and the like.

"Heteroaryl" means an aromatic heterocycle ring of 5- to 10 members and having at least one heteroatom selected from nitrogen, oxygen and sulfur, and containing at least 1 carbon atom, including both mono- and bicyclic ring systems. Representative heteroaryls include (but are not limited to) furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrinidinyl, pyrazinyl, triazinyl, cinnolinyl, phthalazinyl, and quinazolinyl.

"Heteroarylalkyl" means an alkyl having at least one alkyl hydrogen atom replaced with a heteroaryl moiety, such as —CH$_2$pyridinyl, —CH$_2$pyrimidinyl, and the like.

"Heterocycle" (also referred to herein as a "heterocycle ring") means a 5- to 7-membered monocyclic, or 7- to 14-membered polycyclic, heterocycle ring which is either saturated, unsaturated or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring as well as tricyclic (and higher) heterocyclic rings. The heterocycle may be attached via any heteroatom or carbon atom Heterocycles include heteroaryls as defined above. Thus, in addition to the aromatic heteroaryls listed above, heterocycles also include (but are not limited to) morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrrhydropyridinyl, tetrahydroprimidinyl, tetrahydrothiophenyl, tetrahydrothiopyranyl, tetrahydropyrimidinyl, tetmhydrothiophenyl, tetrahydrothiopyranyl, and the like.

"Heterocyclealkyl" means an alkyl having at least one alkyl hydrogen atom replaced with a heterocycle, such as —CH$_2$morpholinyl, and the like.

"Cycloalkyl" means a saturated or unsaturated (but not aromatic) carbocyclic ring containing from 3-8 carbon atoms, such as cyclopentane, cyclohexane, cycloheptane, cyclohexene, and the like.

"Cycloalkylcycloalkyl" means a cycloalkyl ring fused to a cycloalkyl ring, such as decalin.

"Cycloalkylaryl" means a cycloalkyl ring fused to aryl, such as tetran.

"Cycloalkylheterocycle" means a cycloalkyl ring fused to a heterocycle ring.

The term "substituted" as used herein means any of the above groups (eg., alkyl, aryl, arylallyl, heteroaryl, heterdarylalkyl, heterocycle, heterocyclealkyl, etc.) wherein at least one hydrogen atom is replaced with a substituent. In the case of a keto substituent ("—C(═O)—") two hydrogen atoms are replaced. When substituted, "substituents" within the context of this invention include halogen, hydroxy, cyano, nitro, amino, alkylamino, dialkylamino, alkyl, alkoxy, alkylthio, haloalkyl, aryl, substituted aryl, arylalkyl, substituted arylalkyl, heteroaryl, substituted heteroaryl, heteroaxylalkyl, substituted heteroarylalkyl, heterocycle, substituted heterocycle, heterocyclealkyl, substituted heterocyclealkyl, —NR$_a$R$_b$, —NR$_a$C(═O)R$_b$, —NR$_a$C(═O)NR$_a$R$_b$, —NR$_a$C(═O)OR$_b$ —NR$_a$SO$_2$R$_b$, —OR$_a$, —C(═O)R$_a$ —C(═O)OR$_a$, —C(═O)NR$_a$R$_b$, —OC(═O)NR$_a$R$_b$, —SH, —SR$_a$, —SOR$_a$, —S(═O)$_2$R$_a$, —OS(═O)$_2$R$_a$, —S(═O)$_2$OR$_a$, wherein R$_a$ and R$_b$ are the same or different and independently hydrogen, alkyl, haloalkyl substituted allyl, aryl, substituted aryl arylalkyl, substituted arylalkyl, heteroaryl, substituted heteroaryl, heteroarylalkyl, substituted heteroarylalkyl, heterocycle, substituted heterocycle, heterocyclealkyl or substituted heterocyclealkyl.

"Halogen" means fluoro, chloro, bromo and iodo.

"Haloalkyl" means an alkyl having at least one hydrogen atom replaced with halogen, such as trifluoromethyl and the like.

"Alkoxy" means an alkyl moiety attached through an oxygen bridge (i.e., —O-alkyl) such as methoxy, ethoxy, and the like.

"Alkylthio" means an alkyl moiety attached through a sulfur bridge (i.e., —S-alkyl) such as methylthio, ethylthio, and the like.

"Alkylsulfonyl" means an alkyl moiety attached through a sulfonyl bridge (i.e., —SO$_2$-alkyl) such as methylsulfonyl, ethylsulfonyl, and the like.

"Alkylamino" and "dialkylamino" mean one or two alkyl moiety attached through a nitrogen bridge (i.e., —N-alkyl) such as methylamino, ethylamino, dimethylamino, diethylamino, and the like.

"Hydroxyalkyl" means an alkyl substituted with at least one hydroxyl group. "Mono- or di(cycloalkyl)methyl" represents a methyl group substituted with one or two cycloalkyl groups, such as cyclopropylmethyl, dicyclopropylmethyl, and the like.

"Alkylcarbonylalkyl" represents an alkyl substituted with a —C(═O)alkyl group.

"Alkylcarbonyloxyalkyl" represents an alkyl substituted with a —C(═O)Oalkyl group or a —OC(═O)alkyl group.

"Alkyloxyalkyl" represents an alkyl substituted with a —O-alkyl group.

"Alkylthioalkyl" represents a alkyl substituted with a —S-alkyl group.

"Mono- or di(alkyl)amino represents an amino substituted with one alkyl or with two alkyls, respectively.

"Mono- or di(alkyl)aminoalkyl" represents a alkyl substituted with a mono- or di(alkyl)amino.

Depending upon the A, X, Y substituents, representative compounds of this invention include the following structure (II) through (XII):

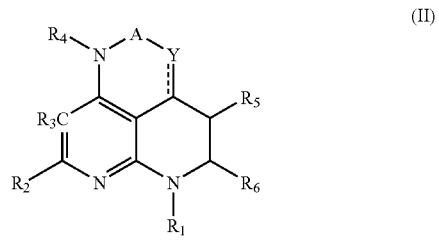

(II)

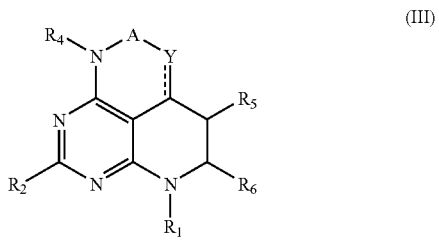

(III)

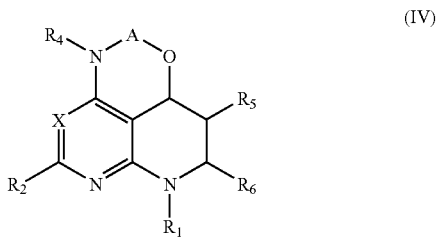

(IV)

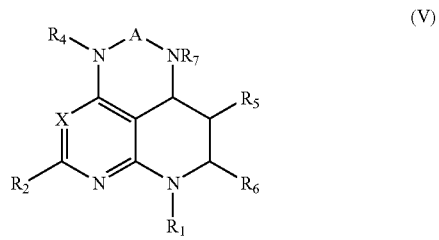

(V)

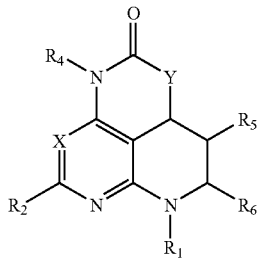 (VI)

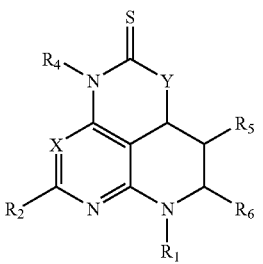 (VII)

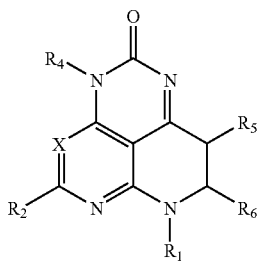 (VIII)

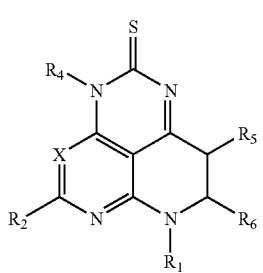 (IX)

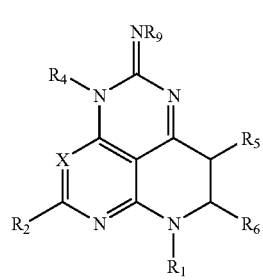 (X)

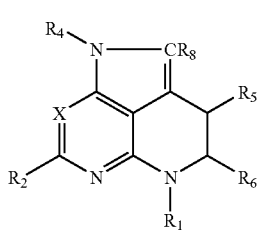 (XI)

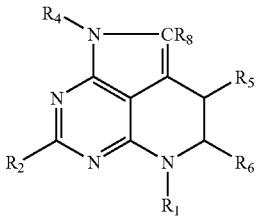 (XIa)

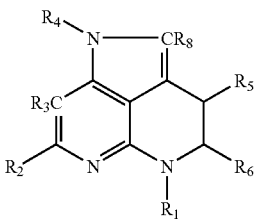 (XIb)

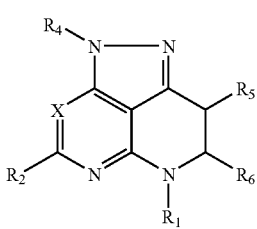 (XII)

In more specific embodiments of this invention, representative $R_1$ groups of this invention include (but are not limited to) 2,4-dichlorophenyl, 2,4-dimethyl-phenyl, 2-chloro-4-methylphenyl, 2-methyl-4-chlorophenyl, 2,4,6-trimethylphenyl, 2-chloro-4-methoxyphenyl, 2-methyl-4-methoxyphenyl, 2,4-dimethoxyphenyl, 2-trifluoromethyl-4-chlorophenyl, 3-methoxy-4-chlorophenyl, 2,5-dimethoxy-4-chlorophenyl, 2-methoxy-4-trichloromethylphenyl, 2-methoxy-4-isopropylphenyl 2-methoxy-4-trifluoromethylphenyl, 2-methoxy-4-isopropylphenyl 2-methoxy-4-methylphenyl, 4-methyl-6-dimethylaminopyridin-3-yl, 4-dimethylamino-6-methyl-pyridin-3-yl, 6-dimethylamino-pyridin-3-yl and 4-diethylamino-pyridin-3-yl.

Similarly, representative $R_2$ groups include hydrogen and alkyl such as methyl and ethyl, while representative $R_3$ groups include hydrogen, halogen such as chlorine, fluorine and bromine, alkyl such as methyl and ethyl, orhaloalkyl such as trifluoromethyl.

Preferred compounds according to the invention are:
7-methyl-1-(1-propyl-butyl)-5-[4-1,1,2-trifluoro-ethyl)-2-trifluoromethylphenyl]1,2,2a,3,4,5-exahydro-1,5,6,8-tetraaza-acenaphtylene (5-1-1);
3-methyl-4-[7-methyl-1-(1-propyl-butyl)-3,4-dihydro-1H-1,5,6,8-tetraaza-acenaphthylen-5-yl]-benzonitrile (5-1-2);
4-[1-(1-ethyl-propyl)-7-methyl-3,4-dihydro-1H-1,5,6,8-tetraaza-acenaphthylen-5-yl]-3-methyl-benzonitrile (5-1-3);
3-chloro-4-[7-methyl-1-(1-propyl-butyl)-3,4-dihydro-1H-1,5,6,8-tetraaza-acenaphthylen-5-yl]-benzonitrile (5-1-4);
3-chloro-4-[1-(1-ethyl-propyl)-7-methyl-3,4-dihydro-1H-1,5,6,8-tetraaza-acenaphthylen-5-yl]-benzonitrile (5-1-5);
5-(2,4-bis-trifluoromethyl-phenyl)-1(1-ethyl-propyl)-7-methyl-1,3,4,5-tetrahydro-1,5,6,8-tetraaza-acenaphthylene (5-1-6);

5-(2,4-bis-trifluoromethyl-phenyl)-7-methyl-1-(1-propyl-butyl)-1,3,4,5-tetrahydro-1,5,6-triaza-acenaphthylene (6-1-1).

The compounds of the present invention may generally be utilized as the free base. Alternatively, the compounds of this invention may be used in the form of acid addition salts. Acid addition salts of the free base amino compounds of the present invention may be prepared by methods well known in the art, and may be formed from organic and inorganic acids.

Suitable organic acids include maleic, malic, fumaric, benzoic, ascorbic, succinic, methanesulfonic, p-toluensulfonic, acetic, oxalic, propionic, tartaric, salicylic, citric, gluconic, lactic, mandelic, cinnamic, aspartic; stearic, palmitic, glycolic, glutamic, and benzenesulfonic acids. Suitable inorganic acids include hydrochloric, hydrobromic, sulfuric, phosphoric, and nitric acids. Thus, the term "pharmaceutically acceptable salt" of structure (I) is intended to encompass any and all acceptable salt forms.

In general, the compounds of structure (I) may be made according to the organic synthesis techniques known to those skilled in this field, as well as by the representative methods set forth in the Examples.

In particular, compounds of formula (XIa) may be prepared according to the following Scheme 1, starting from compounds (XIII), in which the hydroxy group is conveniently protected with a suitable protecting group (Pg), whose preparation is described in the following Examples:

Scheme 1

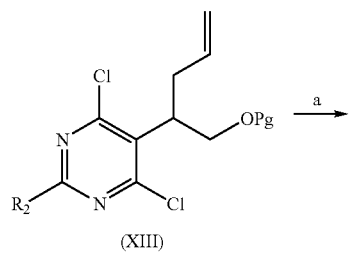

(XIII)

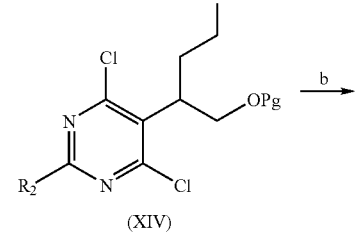

(XIV)

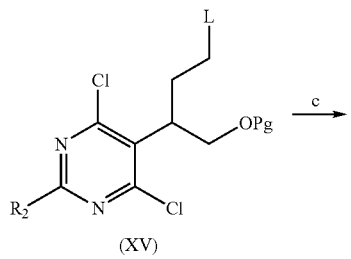

(XV)

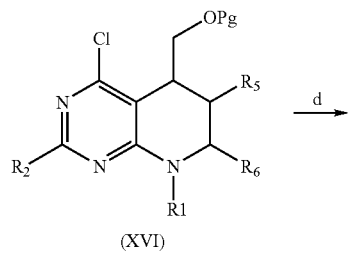

(XVI)

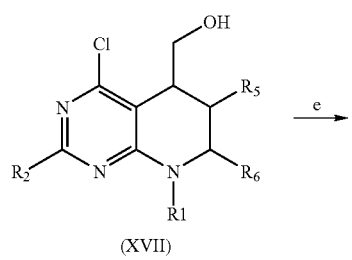

(XVII)

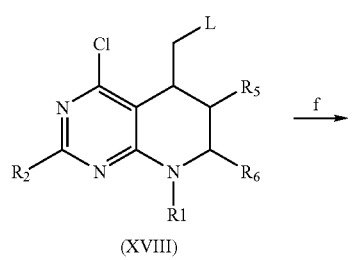

(XVIII)

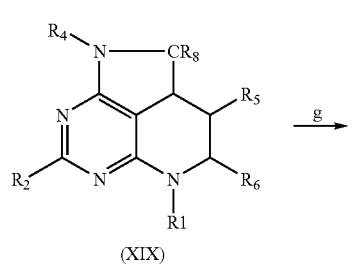

(XIX)

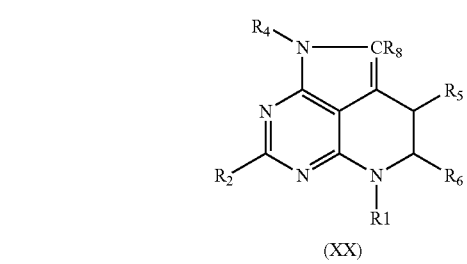

(XX)

in which:
    step a stands for oxidative cleavage of the double bond by, for example, ozonization; followed by reductive work-up;
    step b stands for conversion of the hydroxy group in a leaving group, such as mesylate;
    step c stands for alkylation with the suitable aniline derivative $R_1NH_2$ in strong basic conditions, followed by a "in situ" intramolecular cyclisation;

step d stands for deprotection of the hydroxy protecting group (e.g. Et$_3$N-3HF in DMF at r.t. overnight);

step e stands for conversion of the hydroxy group in a leaving group, such as mesylate;

step f stands for reaction with the suitable amine R$_4$NH$_2$ by heating;

step g stands for dehydrogenation by oxidation with the suitable oxidating agent (e.g.DDQ).

The starting compounds (XIII) may be conveniently prepared according to the following Scheme 2:

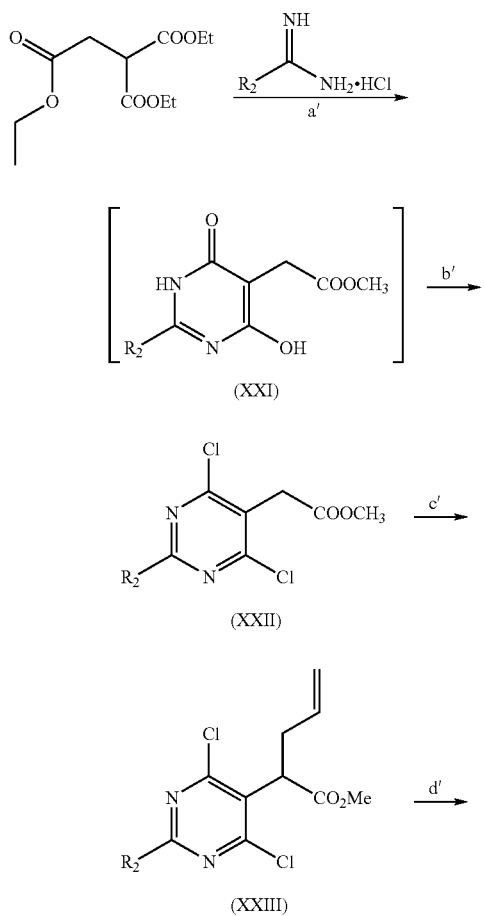

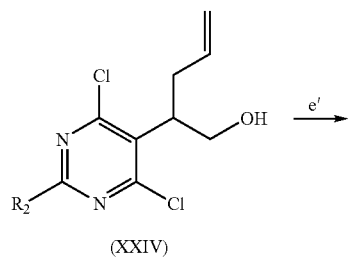

in which step a' stands for reaction with the suitable amidine and intramolecular cyclisation in basic conditions (i.e. MeONa, refluxing toluene);

step b' stands for chlorination (in similar way to what described in Wayne G. C. et al., J. Prakt. Chem., (2000), 342(5), 504-7);

step c' stands for allylation with allyl iodide at 0° C. in basic conditions (e.g. LiHMDS);

step d' stands for reduction of the ester group with a suitable reducing agent, e.g. DIBMAl—H, in usual conditions (CH$_2$Cl$_2$, 0° C. to r.t.);

step e' stands for protection of the hydroxy group, preferably with t-BuPh$_2$SiCl (TBP), in DMF with DMAP as catalyst (0° C. to r.t).

Compounds of formula (XIb) may be conveniently prepared according to the following Scheme 3, starting from compounds of formula (XXV):

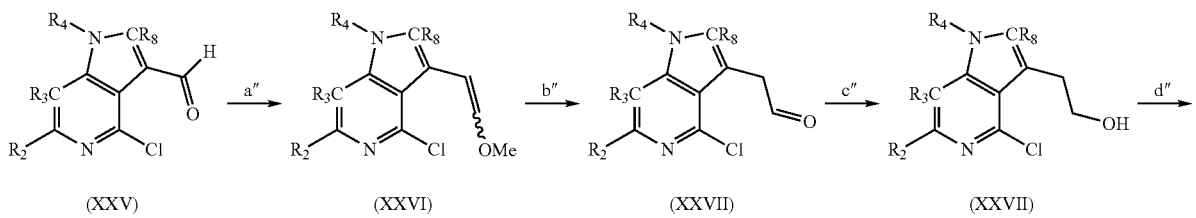

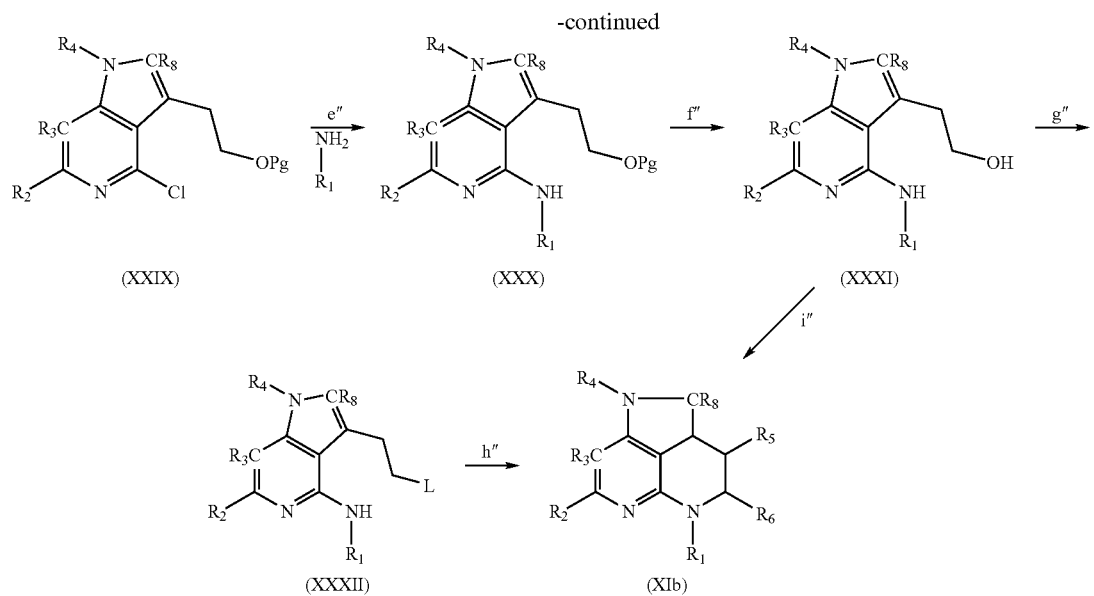

in which:
- step a" stands for homologation of a carbon atom by Wittig reaction with the suitable ylide, in the presence of a suitable organic base like n-BuLi. The reaction is carried out in an aprotic solvent such as acetonitrile or an ether such as tetrahydrofuran;
- step b" stands for usual hydrolysis in acid conditions (e.g. HCl in THF) of the enol ether (XXVI);
- step c" stands for reduction of the aldehyde group by a suitable reducing agent (e.g. NaBH$_4$);
- step d" stands for protection of the hydroxy, preferably with t-BuMe$_2$SiCl (TBS), in DMF with imidazole and DMAP as catalyst (0° C. to r.t);
- step e" stands for microwave assisted Buchwald reaction with the suitable aniline derivative R$_1$NH$_2$;
- step f" stands for deprotection of the hydroxy protecting group (e.g. Et$_3$N-3HF in DMF at r.t. overnight);
- step g" stands for conversion of the hydroxy group in a leaving group, such as mesylate;
- step h" stands for intramolecular cyclisation in basic conditions.

Alternatively, the final compounds (XIb) may be obtained from compounds (XXXI) by intramolecular cyclisation, for example by mesylation of the hydroxy group in basic conditions (i.e. Et$_3$N) followed by in situ cyclisation (step i").

In a preferred embodiment of the invention for the compounds (XIa) and (XIb), R$_3$, R$_5$, R$_6$ and R$_8$ are hydrogen.

Examples of suitable hydroxy protecting group include trihydrocarbyl silyl ethers such as the trimethylsilyl or t-butyldimethylsilyl ether. The hydroxyl protecting groups may be removed by well-known standard procedures (such as those described in Protective Groups in Organic Chemistry, pages 46-119, Edited by J F W McOmie (Plenum Press, 1973)). For example when Rb is a t-butyldimethylsilyl group, this may be removed by treatment with triethylamine trihydrofluoride.

The subject invention also includes isotopically-labeled compounds, which are identical to those recited in formulas I and following, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine, iodine, and chlorine, such as $^3$H, $^{11}$C, $^{14}$C, $^{18}$F, $^{123}$I and $^{125}$I.

Compounds of the present invention and pharmaceutically acceptable salts of said compounds that contain the aforementioned isotopes and/or other isotopes of other atoms are within the scope of the present invention. Isotopically—labeled compounds of the present invention, for example those into which radioactive isotopes such as $^3$H, $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. $^{11}$C and $^8$F isotopes are particularly useful in PET (positron emission tomography), and $^{125}$I are particularly useful in SPECT (single photon emission computerized tomography), all useful in brain imaging. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labeled compounds of formula I and following of this invention can generally be prepared by carrying out the procedures disclosed in the Schemes and/or in the Examples below, by substituting a readily available isotopically labeled reagent for a non-isotopically labeled reagent.

The effectiveness of a compound as a CRF receptor antagonist may be determined by various assay methods. Suitable CRF antagonists of this invention are capable of inhibiting the specific binding of CRF to its receptor and antagonizing activities associated with CRF. A compound of structure (I) may be assessed for activity as a CRF antagonist by one or more generally accepted assays for this purpose, including (but not limited to) the assays disclosed by DeSouza et al. (*J. Neuroscience* 7:88, 1987) and Battaglia et al. (*Synapse* 1:572, 1987). As mentioned above, suitable CRF antagonists include compounds which demonstrate CRF receptor affinity. CRF receptor affinity may be determined by binding studies that measure the ability of a compound to inhibit the binding of a radiolabeled CRF (eg., [$^{125}$I]tyrosine-CFR) to its receptor (e.g., receptors prepared from rat cerebral cortex membranes). The radioligand binding assay described by DeSouza et al. (supra, 1987) provides an assay for determining a compound's affinity for the CRF receptor. Such activity is typically calculated from the $IC_{50}$ as the concentration of a compound necessary to displace 50% of the radiolabeled ligand from the receptor, and is reported as a "$K_i$" value calculated by the following equation:

$$K_i = \frac{IC_{50}}{1 + L/K_D}$$

where L=radioligand and $K_D$=affinity of radioligand for receptor (Cheng and Prusoff, *Biochem. Pharmacol.* 22:3099, 1973).

In addition to inhibiting CRF receptor binding, a compound's CRF receptor antagonist activity may be established by the ability of the compound to antagonize an activity associated with CRF. For example, CRF is known to stimulate various biochemical processes, including adenylate cyclase activity. Therefore, compounds may be evaluated as CRF antagonists by their ability to antagonize CRF-stimulated adenylate cyclase activity by, for example, measuring cAMP levels. The CRF-stimulated adenylate cyclase activity assay described by Battaglia et al. (supra, 1987) provides an assay for determining a compound's ability to antagonize CRF activity. Accordingly, CRF receptor antagonist activity may be determined by assay techniques which generally include an initial binding assay (such as disclosed by DeSouza (supra, 1987)) followed by a cAMP screening protocol (such as disclosed by Battaglia (supra, 1987)).

With reference to CRF receptor binding affinities, CRF receptor antagonists of this invention have a $K_i$ of less than 10 µM. In a preferred embodiment of this invention, a CRF receptor antagonist has a $K_i$ of less than 1 µM, and more preferably less than 0.25 µM (ie., 250 nM). As set forth in greater detail below, the $K_i$ values of representative compounds of this invention may be assayed by the methods set forth in Example 7.

The CRF receptor antagonists of the present invention demonstrate activity at the CRF receptor site, and may be used as therapeutic agents for the treatment of a wide range of disorders or illnesses including endocrine, psychiatric, and neurologic disorders or illnesses. More specifically, the CRF receptor antagonists of the present invention may be useful in treating physiological conditions or disorders arising from the hypersecretion of CRF. Because CRF is believed to be a pivotal neurotransmitter that activates and coordinates the endocrine, behavioral and automatic responses to stress, the CRF receptor antagonists of the present invention can be used to treat neuropsychiatric disorders. Neuropsychiatric disorders which may be treatable by the CRF receptor antagonists of this invention include affective disorders such as depression; anxiety-related disorders such as generalized anxiety disorder, panic disorder, obsessive-compulsive disorder, abnormal aggression, cardiovascular abnormalities such as unstable angina and reactive hypertension; and feeding disorders such as anorexia nervosa, bulimia, and irritable bowel syndrome (IBS). CRF antagonists may also be useful in treating stress-induced immune suppression associated with various diseases states, as well as stroke. Other uses of the CRF antagonists of this invention include treatment of inflammatory conditions (such as rheumatoid arthritis, uveitis, asthma, inflammatory bowel disease (IBD) and G.I. motility), Cushing's disease, infantile spasms, epilepsy and other seizures in both infants and adults, and various substance abuse and withdrawal (including alcoholism).

In another embodiment of the invention, pharmaceutical compositions containing one or more CRF receptor antagonists are disclosed. For the purposes of administration, the compounds of the present invention may be formulated as pharmaceutical compositions. Pharmaceutical compositions of the present invention comprise a CRF receptor antagonist of the present invention (i.e., a compound of structure (I)) and a pharmaceutically acceptable carrier and/or diluent. The CRF receptor antagonist is present in the composition in an amount which is effective to treat a particular disorder—that is, in an amount sufficient to achieve CRF receptor antagonist activity, and preferably with acceptable toxicity to the patient. Preferably, the pharmaceutical compositions of the present invention may include a CRF receptor antagonist in an amount from 0.1 mg to 250 mg per dosage depending upon the route of administration, and more preferably from 1 mg to 60 mg. Appropriate concentrations and dosages can be readily determined by one skilled in the art.

Pharmaceutically acceptable carrier and/or diluents are familiar to those skilled in the art. For compositions formulated as liquid solutions, acceptable carriers and/or diluents include saline and sterile water, and may optionally include antioxidants, buffers, bacteriostats and other common additives. The compositions can also be formulated as pills, capsules, granules, or tablets which contain, in addition to a CRF receptor antagonist, diluents, dispersing and surface active agents, binders, and lubricants. One skilled in this art may further formulate the CRF receptor antagonist in an appropriate manner, and in accordance with accepted practices, such as those disclosed in *Remington's Pharmaceutical Sciences*, Gennaro, Ed, Mack Publishing Co., Easton, Pa. 1990.

In addition, prodrugs are also included within the context of this invention. Prodrugs are any covalently bonded carriers that release a compound of structure (I) in vivo when such prodrug is administered to a patient. Prodrugs are generally prepared by modifying functional groups in a way such that the modification is cleaved, either by routine manipulation or in vivo, yielding the parent compound.

With regard to stereoisomers, the compounds of structure (I) may have chiral centers and may occur as racemates, racemic mixtures and as individual enantiomers or diastereomers. All such isomeric forms are included within the present invention, including mixtures thereof. Furthermore, some of the crystalline forms of the compounds of structure (I) may exist as polymorphs, which are included in the present invention. In addition, some of the compounds of structure (I) may also form solvates with water or other organic solvents. Such solvates are similarly included within the scope of this invention.

In another embodiment, the present invention provides a method for treating a variety of disorders or illnesses, including endocrine, psychiatric and neurologic disorders or illnesses. Such methods include administering of a compound of the present invention to a warm-blooded animal in an amount sufficient to treat the disorder or illness. Such methods include systemic administration of a CRF receptor antagonist of this invention, preferably in the form of a pharmaceutical composition. As used herein, systemic administration includes oral and parenteral methods of administration. For oral administration, suitable pharmaceutical compositions of CRF receptor antagonists include powders, granules, pills, tablets, and capsules as well as liquids, syrups, suspensions, and emulsions. These compositions may also include flavorants, preservatives, suspending, thickening and emulsifying agents, and other pharmaceutically acceptable additives. For parental administration, the compounds of the present invention can be prepared in aqueous injection solutions which may contain, in addition to the CRF receptor antagonist, buffers, antioxidants, bacteriostats, and other additives commonly employed in such solutions.

As mentioned above, administration of a compound of the present invention can be used to treat a wide variety of disorders or illnesses. In particular, the compounds of the present invention may be administered to a warm-blooded animal for the treatment of depression, anxiety disorder, panic disorder, obsessive-compulsive disorder, abnormal aggression, unstable angina, reactive hypertension, anorexia nervosa, bulimia, irritable bowel syndrome (IBS), inflammatory bowel disease (IBD), stress-induced immune suppression, stroke, inflammation, Cushing's disease, infantile spasms, epilepsy, and substance abuse or withdrawal.

The following examples are provided for purposes of illustration, not limitation.

EXAMPLES

The CRF receptor antagonists of this invention may be prepared by the methods disclosed in Examples 1 through 6. Example 7 presents a method for determining the receptor binding activity ($K_i$), and Example 8 discloses an assay for screening compounds of this invention for CRF-stimulated adenylate cyclase activity.

In the Intermediates and Examples unless otherwise stated:

Melting points (m.p.) were determined on a Gallenkamp m.p. apparatus and are uncorrected. All temperatures are expressed as °C. Infrared spectra were measured on a FT-IR instrument Proton Magnetic Resonance ($^1$H-NMR) spectra were recorded at 400 Mz, chemical shifts are reported in ppm downfield (d) from Me$_4$Si, used as internal standard, and are assigned as singlets (s), doublets (d), doublets of doublets (dd), triplets (t), quartets (q) or multiplets (m). Column chromatography was carried out over silica gel (Merck AG Darmstaadt, Germany). The following abbreviations are used in text: EtOAc=ethyl acetate, cHex=cyclohexane, CH$_2$Cl$_2$=dichloromethane, Et$_2$O=dietyl ether, DDQ=2,3-dichloro-5,6-dicyano-1,4-benzoquinone; DMF=N,N-dimethylformamide, DIPEA=N,N-diisopropyl-ethylamine, MeOH=methanol, Et$_3$N=triethylamine, TBS=ter-butyldimethylsilyl; TBP=ter-butyldiphenylsilyl; TFA=trifluoroacetic acid, THF=tetrahydrofuran, DIBAL-H=diisobutylaluminium hydride, DMAP=dimethylaminopyridine, LHMDS=lithium hexamethyldisilazane; Tlc refers to thin layer chromatography on silica plates, and dried refers to a solution dried over anhydrous sodium sulphate; r.t. (RT) refers to room temperature.

Example 1

Synthesis of Representative Pyridine Intermediate

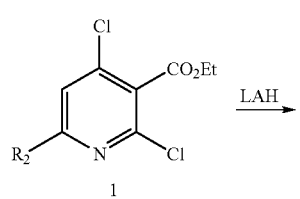

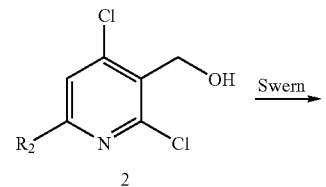

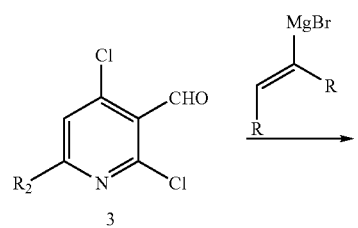

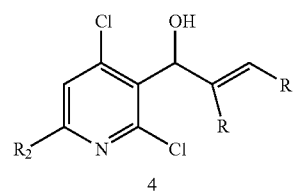

Compound 2

Chloropyridine 1 is dissolved in THF and added to a stirred suspension of LAH in THF at −78° C. The mixture is stirred for 6 hours at this temperature and for 1 hour at −30° C. The mixture is then treated cautiously with water, 15% aqueous NaOH and water with vigorous stiring. The mixture is warmed to room temperature and filtered. The white precipitate is washed liberally with ethyl acetate. The combined organic portions are dried (MgSO$_4$) and concentrated under vacuum. Purification via flash chromatography gives the desired 2.

Compound 3

DMSO (6 equivalents) is added to a stirred solution of oxalyl chloride (3 equivalents) in dichloromethane at −70° C. After 15 min, alcohol 2 (1 equivalent) in dichloromethane is added, followed by triethylamine. The mixture is allowed to warm to room temperature and stirred for 1 hour. The mixture is washed with aqueous sodium bicarbonate (75 mL), dried (MgSO$_4$), and concentrated under vacuum. Purification via flash chromatography gives the desired product 3.

Compound 4

Alkenylmagnesium bromide in THF (1 equivalent) is added to a stirred solution of aldehyde 3 (1 equivalent) in THF at −78° C. The mixture is stirred at this temperature for 30 minutes, warmed to room temperature and quenched with aqueous sodium bicarbonate. The mixture is then extracted with ethyl acetate and the combined extracts are dried (MgSO$_4$) and concentrated under vacuum. Purification via flash chromatography gives the desired 4.

Example 2

Synthesis of Representative Pyrimidine Intermediate

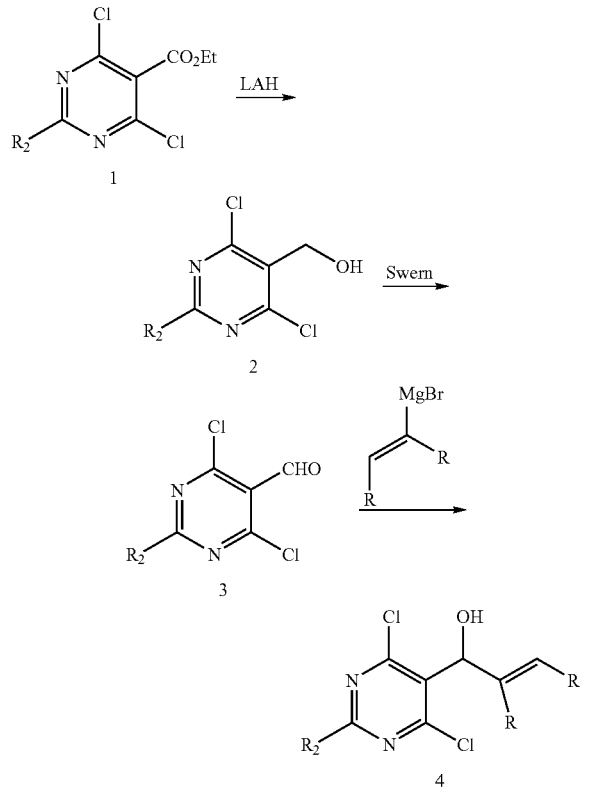

Example 3

Synthesis of Representative Compounds of Structure (1)

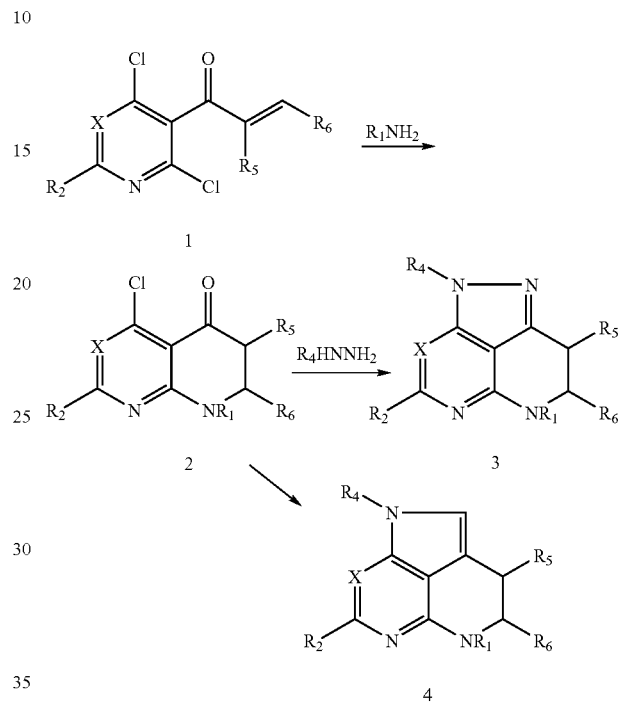

Compound 2

The chloropyrimidine 1 is dissolved in THF and added to a stirred suspension of LAH in THF at −78° C. The mixture is stirred or 6 hours at this temperature and for 1 hour at −30° C. The mixture is then treated cautiously with water, 15% aqueous NaOH and water with vigorous stirring. The mixture is warmed to room temperature and filtered. The white precipitate is washed liberally with ethyl acetate. The combined organic portions are dried (MgSO$_4$) and concentrated under vacuum. Purification via flash chromatography gives the desired product 2.

Compound 3

DMSO (6 equivalents) is added to a stirred solution of oxalyl chloride (3 equivalents) in dichloromethane at −70° C. After 15 min, alcohol 2 (1 equivalent) in dichloromethane is added, followed by triethylamine. The mixture is allowed to warm to room temperature and stirred for 1 hour. The mixture is washed with aqueous sodium bicarbonate (75 mL), dried (MgSO$_4$), and concentrated under vacuum. Purification via flash chromatography gives the desired product 3.

Compound 4

Alkenylmagnesium bromide in THF (1 equivalent) is added to a stirred solution of aldehyde 3 (1 equivalent) in THF at −78° C. The mixture is stirred at this temperature for 30 minutes, warmed to room temperature and quenched with aqueous sodium bicarbonate. The mixture is extracted with ethyl acetate and the combined extracts are dried (MgSO$_4$) and concentrated under vacuum. Purification via flash chromatography gives the desired product 4.

Compound 2:

The enone 1 (compound 4 from examples 1 and 2 above, 4.26 mmol), R$_1$NH$_2$ (4.3 mmol) and toluenesulfonic acid monohydrate (4.3 mmol) in ethanol (20 mL) are heated at 60° C. for 16 hours. The mixture is concentrated, taken up in ethyl acetate (50 mL), washed with aq. NaHCO$_3$ (20 mL), dried (MgSO$_4$) and concentrated under vacuum. The residue is purified on a silica gel column (elution with 25% ethyl acetate in hexanes) to afford 2.

Compound 4:

LDA in THF (0.325M, 0.83 mL, 0.27 mmol) is added to a stirred solution of the phosphine oxide (66 mg, 0.27 mmol) in THF (2 mL) at −25° C. After 15 minutes, compound 2 (11 mg, 0.034 mmol) in THF (1 mL) is added and the mixture is stirred for 15 min. NaH (30 mg) is added, the mixture is warmed to room temperature and stirred for 16 hours. The mixture is diluted with water (15 mL) and extracted with EtOAc (4×10 mL). The combined extracts are dried (MgSO4), concentrated in vacuo and the residue is purified by preparative TLC (elution with 30% EtOAc/Hex.) to afford an oil which is then treated with TsOH.H$_2$O (4.2 mg, 0.022 mmol) and R$_4$NH$_2$ (0.085 mmol) at 130° C. for 16 hours. The mixture is cooled to room temperature, diluted with aq. NaHCO$_3$ (2 mL) and extracted with EtOAc (4×2 mL). The combined extracts are dried (MgSO$_4$), concentrated in vacuo and the residue is purified by preparative TLC to afford compound 4.

Compound 3:

Compound 2 (68 mg, 0.23 mmol) and R₄HNNH₂ (0.35 mmol) are heated at 140° C. for 5 hours. The mixture is cooled to room temperature, diluted with aq. NaHCO₃ (2 mL) and extracted with EtOAc (4×2 mL). The combined extracts are dried (MgSO₄), concentrated in vacuo, and the residue is purified by prep TLC (elution with 30% EtOAc/hexane) to afford compound 3.

Example 4

Synthesis of Representative Compounds of Structure (I)

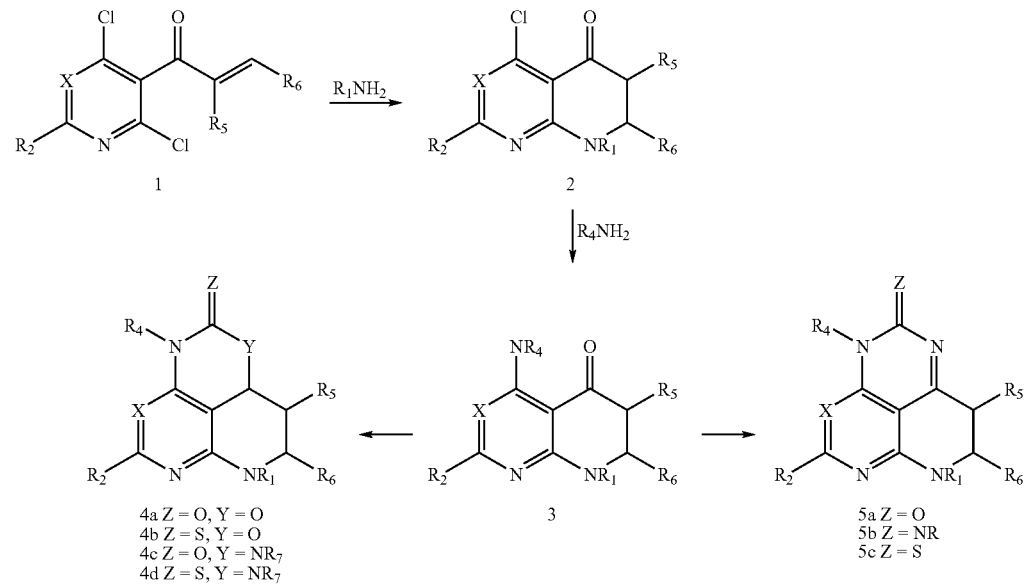

Compound 2

The enone 1 (compound 4 from examples 1 and 2, 4.26 mmol), R₁NH₂ (4.3 mmol) and toluenesulfonic acid monohydrate (4.3 mmol) in ethanol (20 mL) are heated at 60° C. for 16 hours. The mixture is concentrated, taken up in ethyl acetate (50 mL), washed with aq. NaHCO₃ (20 mL), dried (MgSO₄) and concentrated under vacuum. The residue is purified on a silica gel column (elution with 25% ethyl acetate in hexanes) to afford 2.

Compound 3:

Ketone 2 (0.16 mmol), p-toluenesulfonic acid monohydrate (30 mg, 0.16 mmol) and R₄NH₂ (0.18 mmol) are dissolved in ethanol (0.5 mL) and heated at 80° C. in a sealed tube for 20 hours. The mixture is cooled to room temperature, diluted with aq. NaHCO₃ (2 mL), and extracted with ethyl acetate (4×2 mL). The combined organic extracts are dried (MgSO₄), concentrated under vacuum, and the residue is purified by preparative TLC to afford 3.

Compound 4a: (Z=O, Y=O)

Ketone 3 (0.095 mmol) is dissolved in methanol (1 mL) and treated with sodium borohydride (25 mg, 0.66 mmol). The mixture is stirred for 4 hours, diluted with aq. NaHCO₃ (2 mL), and extracted with ethyl acetate (4×2 mL). The combined organic extracts are dried (MgSO₄), concentrated under vacuum, and the residue is taken up in toluene (1 mL) and treated with a solution of phosgene in toluene (20%, 0.1 mL). After 16 hours, the solution is concentrated under vacuum and the residue is purified by preparative TLC to afford 32 mg (75%) of carbonate 4a as a yellow oil.

Compound 4b: (Z=S, Y=O)

Ketone 3 (0.095 mmol) is dissolved in methanol (1 mL) and treated with sodium borohydride (25 mg, 0.66 mmol). The mixture is stirred for 4 hours, diluted with aq. NaHCO₃ (2 mL), and extracted with ethyl acetate (4×2 mL). The combined organic extracts are dried (MgSO₄), concentrated under vacuum, and the residue is taken up in toluene (1 mL) and treated with a solution of thiophosgene in toluene (20%, 0.1 mL). After 16 hours, the solution is concentrated under vacuum and the residue is purified by preparative TLC to afford 25 mg (55%) of 7b as a yellow oil.

Compound 4c: (Z=O, Y=NR₇)

Ketone 3 (0.095 mmol) and amine (0.20 mL) are dissolved in acetonitrile (1 mL) and are treated with sodium cyanoborohydride (25 mg). Acetic acid (1 drop) is added and the mixture is stirred for 4 hours, diluted with aq. NaHCO₃ (2 mL), and extracted with ethyl acetate (4×2 mL). The combined organic extracts are dried (MgSO₄), concentrated under vacuum, and the residue is taken up in toluene (1 mL) and treated with a solution of phosgene in toluene (20%, 0.1 mL). After 18 hours, the solution is concentrated under vacuum and the residue is purified by preparative TLC to afford urea 4c.

Compound 4d: (Z=S, Y=NR₇)

Ketone 3 (0.095 mmol) and amine (0.20 mL) are dissolved in acetonitrile (1 mL) and are treated with sodium cyanoborohydride (25 mg). Acetic acid (1 drop) is added and the mixture is stirred for 4 hours, diluted with aq. NaHCO₃ (2 mL), and extracted with ethyl acetate (4×2 mL). The combined organic extracts are dried (MgSO₄), concentrated under vacuum, and the residue is taken up in toluene (1 mL) and treated with a solution of thiophosgene in toluene (20%, 0.1 mL). After 18 hours, the solution is concentrated under vacuum and the residue is purified by preparative TLC to afford thiourea 4d Compound 5a: (Z=O)

Ketone 3 (0.16 mmol), urea (30 mg) and ZnCl₂ (25 mg) are heated at 200° C. for 5 h. The mixture is cooled to room temperature, diluted with aq. NaHCO$_3$ (2 mL), and extracted with ethyl acetate (4×2 mL). The combined organic extracts are dried (MgSO$_4$), concentrated under vacuum, and the residue is purified by preparative TLC to afford urea 5a.

Compound 5b: (Z=NR$_9$)

The urea from the above procedure (5a, 0.070 mmol) and PCl$_5$ (15 mg, 0.070 mmol) are heated in toluene at 90° C. for 3 hours during which time a white solid forms. The mixture is cooled to room temperature and is treated with amine (0.10 mL). Stirring is continued for 30 minutes. The mixture is diluted with aq. NaHCO$_3$ (2 mL), and extracted with ethyl acetate (4×2 mL). The combined organic extracts are dried (MgSO$_4$), concentrated under vacuum, and the residue is purified by preparative TLC to afford guanidine 5b.

Compound 5c: (Z=S)

The urea from the above procedure (5a, 0.070 mmol) and P$_4$S$_{10}$ (50 mg) are heated in toluene at 90° C. for 20 hours. The mixture is cooled to room temperature, diluted with aq. NaHCO$_3$ (2 mL), and extracted with ethyl acetate (4×2 mL). The combined organic extracts are dried (MgSO$_4$), concentrated under vacuum, and the residue is purified by preparative TLC to afford thiourea 5c.

Example 5

Synthesis of Representative Compounds of Structure (XIa)

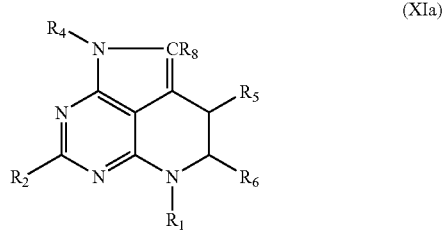

(XIa)

Intermediate 1

(4,6-Dichloro-2-methyl-pyrimidin-5-yl)-acetic acid methyl ester

Sodium (1.74 g, 3 eq) was added portionwise to anh. MeOH (60 mL), at 0° C., under N$_2$. After consumption of metallic sodium, acetamidine hydrochloride (7.06 g, 3 eq) was added. After 20 min. of stirring, the precipitated NaCl was filtered off. A solution of 2-ethoxycarbonyl-succinic acid diethyl ester (6.04 g, 24.5 mmol) in anhydrous MeOH (20 mL) was added to the solution of free acetamidine and the mixture was stirred at r.t. for 2 days. The reaction mixture was concentrated to dryness in vacuo and the yellow foam (8.69 g) obtained was then mixed with POCl$_3$ (70 mL) and heated at reflux for 3.5 hr. The resulting solution was cooled to room temperature and poured slowly into ice/water (600 mL) and NH$_4$OH (50 mL) with vigorous stirring. The product was extracted with EtOAc (3×50 mL) and with Et$_2$O (3×20 mL). The combined organic extracts were washed with H$_2$O (60 mL) and brine (40 mL), dried over Na$_2$SO$_4$, filtered and concentrated in vacuo. The crude oil was purified by flash chromatography (silica gel, cHex/AcOEt 9:1). Intermediate 1 was obtained as a yellow solid (4.27 g, 73%)

NMR ($^1$H, CDCl$_3$): δ 5.85 (m, 1H), 5.15 (dq, 1H), 5.11 (dq, 1H), 3.61 (dt, 2H), 2.67 (s, 3H). MS (m/z): 202 [M]$^+$.2Cl; 167 [MH—Cl]$^+$, 1Cl.

Intermediate 2

2-(4,6-Dichloro-2-methyl-pyrimidin-5-yl)-pent-4-enoic acid methyl ester

To a solution of intermediate 1 (3 g, 1 eq) in anh. THF (60 mL), at −78° C., under N$_2$, LiHMDS (1M in THF) (16.03 mL, 1.25 eq) was added dropwise. The reaction mixture was cooled at 0° C. and stirred for 30 min. The reaction mixture was cooled at −78° C. and allyl iodide (1.58 mL, 1.35 eq) was added dropwise in 1.5 h. The reaction mixture was stirred at r.t. for 3 h. Then water (30 mL) was added and reaction mixture was extracted with EtOAc (3×60 mL). The organic layers were gathered and washed with sat.aq. NaCl (1×20 mL) and dried over anh. Na$_2$SO$_4$. The solids were filtered and the solvent evaporated to give a crude product, which was purified by flash chromatography (silica gel, 5% EtOAc/Cyclohexane). Intermediate 2 was obtained as a white solid (2.4 g, 8.76 mmol, 68%)

NMR ($^1$H, CDCl$_3$): δ 5.77 (m, 1H), 5.03 (m, 2H), 4.43 (dd, 1H), 3.76 (s, 3H), 3.12 (m, 1H), 2.78 (m, 1H), 2.73 (s, 3H). MS (m/z): 275 [MH]$^+$

Intermediate 3

2-(4,6-Dichloro-2-methyl-pyrimidin-5-yl)-pent-4-en-1-ol

To a solution of intermediate 2 (257 mg, 0.937 mmol) in anh. CH$_2$Cl$_2$ (9.3 ml), at −78° C., under N$_2$, was added DI (1M solution in hexane, 5.6 mL, 6 eq). After the DIBAl-H addition the reaction mixture was stirred at −78° C. for 1 hr and 2 hr at 0° C. The reaction mixture was poured into a solution of HCl 0.5N in ice (20 ml) and extracted with CH$_2$Cl$_2$ (3×10 mL). The combined organic extracts were dried over Na$_2$SO$_4$, filtered and concentrated in vacuo. 200 mg of intermediate 3 was obtained as a colourless oil (yield 86%).

NMR ($^1$H, CDCl$_3$): δ 5.76 (m, 1H), 5.12 (m, 1H), 5.01 (m, 1H), 4.16 (m, 1H), 4.06 (m, 1H), 3.91 (m, 1H), 2.8-2.6 (m, 2H), 2.70 (s, 3H), 1.50 (t, 1H). MS (m/z): 247 [M]$^+$, 2Cl

Intermediate 4

5-[1-(tert-Butyl-diphenyl-silanyloxymethyl)-but-3-enyl]4,6-dichloro-2-methyl-pyrimidine To a solution of intermediate 3 (152 mg, 0.61 mmol) in anh. DMF (4 ml), at 0° C., under N$_2$, was added 4-DMAP (3.8 mg, 0.05 eq), imidazole (420 mg, 10 eq) and Ph$_2$tBuSiCl (0.32 mL, 2 eq). The reaction mixture was stirred at r.t. for 2 hr. To this solution were added 5 ml of sat.aq. NH$_4$Cl in water and the mixture was extracted with Et$_2$O (2×15 ml). The combined organic extracts were washed once with water, once with brine and dried over Na$_2$SO$_4$. The solids were filtered, the solvent was evaporated and the crude yellow oil was purified by flash chromatography (silica gel, cHex/EtOAc 95:5). Intermediate 4 was obtained as a colourless oil (270 mg, 0.55 mmol, 90%).

NMR ($^1$H, CDCl$_3$): δ 7.65 (dd, 2H), 7.56 (dd, 2H), 7.49-7.36 (m, 6H), 5.67 (m, 1H), 5.03 (dd, 1H), 4.94 (dd, 1H), 4.17 (m, 1H), 4.00 (m, 2H), 2.70 (s, 3H), 2.69 (m, 1H), 2.55 (m, 1H), 0.98 (s, 9H). MS (m/z): 485 [MH]$^+$, 2Cl.

Intermediate 5

4-(tert-Butyl-diphenyl-silanyloxy)-3-(4,6-dichloro-2-methyl-pyrimidin-5-yl)-1-ol To a solution of intermediate 4 (1.52 g, 3.14 mmol) in anh. $CH_2Cl_2$/MeOH mixture (4/1 v/v, 50 mL), at −78° C., $O_3$ was bubbled for 15 min while stirring. The reaction mixture was diluted with anh. MeOH (10 mL) and $NaBH_4$ (475 mg, 4 eq) was added, at −78° C. The reaction mixture was stirred at r.t. for 3 hr, then quenched with sat.aq. $NH_4Cl$ (15 mL) and the product was extracted with EtOAc (3×60 mL). The combined organic layers were washed with sat.aq. NaCl (1×20 mL) and dried over anh. $Na_2SO_4$. The solids were filtered and the solvent evaporated to give a crude product, which was purified by flash chromatography (silica gel, cHex/EtOAc 8:2). Intermediate 5 was obtained as a yellow oil (1.14 g, 2.34 mmol, 74%).

NMR ($^1$H, DMSO): δ 7.55-7.33 (, 10H), 4.46 (t, 1H), 4.09,397,2.92 (m, 3H), 3.40-3.20 (m, 2H), 2.00-1.76 (m, 2H), 2.56 (s, 3H), 0.84 (s, 9H). MS (m/z): 489 [MH]$^+$.

Intermediate 6

Methanesulfonic acid 4-(tert-butyl-diphenyl-silanyloxy)-3-(4,6-dichloro-2-methyl-pyrimidin-5-yl)-butyl ester To a solution of intermediate 5 (1.14 g, 2.33 mmol) in anh. $CH_2Cl_2$ (46 mL), at 0° C., $Et_3N$ (1.6 mL, 5 eq) and MsCl (378 μL, 2.1 eq) were added. The reaction mixture was stirred at r.t. for 30 min. Then water (15 mL) was added and reaction mixture was extracted with $CH_2Cl_2$ (3×60 mL). The combined organic layers were washed with sat.aq. NaCl (1×20 mL) and dried over anh. $Na_2SO_4$. The solids were filtered and the solvent evaporated to give a crude product, which was purified by flash chromatography (silica gel, cHex/EtOAc 8:2). Intermediate 6 was obtained as a yellow oil (1.28 g, 2.26 mmol, 97%).

NMR ($^1$H, DMSO): δ 7.60-7.30 (m, 10H), 4.20,4.10-3.90 (m,m, 5H), 3.07 (s, 3H), 2.57 (s, 3H), 2.34-2.06 (m, 2H), 0.84 (s, 9H). MS (m/z): 567 [MH]$^+$.

Intermediate 7

5-(tert-Butyl-diphenyl-silanyloxymethyl)-4-chloro-2-methyl-8-[4-(1,1,2-trifluoro-ethyl)-2-trifluoromethyl-phenyl]-5,6,7,8-tetrahydro-pyrido[2,3-d]pyrimidine To a solution of 2,4-bis(trifluoromethyl)aniline (15.6 mg, 1 eq) in anh. DMF (1 mL), at 0° C., NaH 80%/oil (4.5 mg, 2.2 eq) was added. The reaction mixture was stirred at 0° C. for 15 min then at r.t. for 15 min. The reaction mixture was cooled at 0° C. and a solution of intermediate 6 (38.7 mg, 0.068 mmol) in anh. DMF (0.3 mL) was added. The reaction mixture was stirred at r.t. for 1.5 hr. Then water (2 mL) was added and the reaction mixture was extracted with EtOAc (3×7 mL). The combined organic layers were washed with sat.aq. NaCl (1×10 mL) and dried over anh. $Na_2SO_4$. The solids were filtered and the solvent evaporated to give a crude product, which was purified by flash chromatography (silica gel, cHex/EtOAc 9:1). Intermediate 7 was obtained as a yellow oil (19.4 mg, 0.029 mmol, 43%).

NMR ($^1$H, CDCl$_3$): δ 7.98,7.94 (d,d, 1H), 7.88,7.80 (dd,dd, 1H), 7.77-7.58, 7.44-7.32 (m,m, 3H), 7.35,7.14 (d,d, 1H), 3.98,3.94 (dd, dd, 1H), 3.73,3.55 (t,m, 1H), 3.63,3.59 (m,m, 1H), 3.44-3.36 (m, 2H), 3.38-3.30 (m, 2H), 2.55,2.40 (m,m, 1H), 2.17,2.15 (s,s 1H), 2.04,1.90 (m,m, 1H), 0.98 (s, 9H). MS (m/z): 664 [MH]$^+$.

Intermediate 8

{4-Chloro-2-methyl-8-[4-(1,1,2-trifluoro-ethyl)-2-trifluoromethyl-phenyl]-5,6,7,8-tetrahydro-pyrido[2,3-d]pyrimidin-5-yl}-methanol To a solution of intermediate 7 (52 mg, 0.078 mmol) in anh. DMF (1 mL), at r.t., under $N_2$, $Et_3N.3HF$ (102 μL, 8 eq.) was added and the reaction mixture was stirred at r.t. overnight. It was then diluted with water (2 mL) and extracted with $Et_2O$ (3×5 mL). The combined organic layers were washed with sat.aq. NaCl (1×7 mL) and dried over anh. $Na_2SO_4$. The solids were filtered and the solvent evaporated: The crude product was purified by flash chromatography (silica gel, cHex/EtOAc 6:4). Intermediate 8 was obtained as a clear oil (27 mg, 0.063 mmol, 81%).

NMR ($^1$H, DMSO): δ 8.26-8.12 (m, 2H), 7.90-7.80 (d, 1H), 5.08-4.98 (t, 1H), 3.90-3.60 (2H), 3.70-3.30 (2H), 3.24-3.10 (1H), 2.30 (m, 1H), 2.09 (s, 3H), 2.00-1.80 (m, 1H). MS (m/z): 425 [MH]$^+$.

Intermediate 9

Methanesulfonic acid 4-chloro-2-methyl-8-[4-(1,1,2-trifluoro-ethyl)-2-trifluoromethyl-phenyl]-5,6,7,8-tetrahydro-pyrido[2,3-d]pyrimidin-5-yl-methyl ester To a solution of intermediate 8 (130 mg, 0.306 mmol) in anh. $CH_2Cl_2$ (4 mL), at 0° C., $Et_3N$ (213 μL, 5 eq) and MsCl (50 μL, 2.1 eq) were added. The reaction mixture was stirred at r.t. for 3 hr. Then water (8 mL) was added and the reaction mixture was extracted with $CH_2Cl_2$ (3×20 mL). The combined organic layers were washed with sataq. NaCl (1×10 mL) and dried over anh. $Na_2SO_4$. The solids were filtered and the solvent evaporated to give a crude product, which was purified by flash chromatography (silica gel, cHex/EtOAc 65/35). Intermediate 9 was obtained as a clear oil (138 mg, 0.274 mmol, 90%).

NMR ($^1$H, DMSO): δ 8.30-8.14 (m, 2H), 7.95-7.80 (d,d, 1H), 4.56-4.20 (2H), 3.9-3.4 (m, 3H), 3.25 (s, 3H), 2.11 (s, 3H), 2.2-1.9 (m, 2H). MS (m/z): 425 [MH]$^+$.

Intermediate 10

7-Methyl-1-(1-propyl-butyl)-5-[4-(1,1,2-trifuoro-ethyl)-2-trifluoromethyl-phenyl]-1,2,2a,3,4,5-hexahydro-1,5,6,8-tetraaza-acenaphthylene A mixture of intermediate 9 (135 mg, 0.27 mmol) and heptyl amine (0.5 mL, 12 eq.) was heated at 130° C. (screw cap vial, sand bath) for 3 hr. The reaction mixture was then cooled down to r.t. and diluted with $CH_2Cl_2$ (3 mL). The solvent was evaporated and the crude product was purified by flash chromatography (silica gel, cHex/EtOAc 9:1). Intermediate 10 was obtained as a yellow solid (29.4 mg, 0.06 mmol, 23%).

NMR ($^1$H, CDCl$_3$): δ 7.99 (s, 1H), 7.83 (d, 1H), 7.48 (d, 1H), 4.06-3.24 (bm, 5H), 2.23-2.2 (bm, 4H), 1.74-1.1 (bm, 10H), 0.97 (t, 3H), 0.91 (t, 3H). MS (m/z): 487 [MH]$^+$.

Intermediate 11

4-[5-(tert-Butyl-diphenyl-silanyloxymethyl)-4-chloro-2-methyl-6,7-dihydro-5H-pyrido[2,3-d]pyrimidin-8-yl]-3-methyl-benzonitrile To a solution of 4-amino-3-methylbenzonitrile (14 mg, 0.106 mmol) in DMF (3.5 mL), at 0° C., under $N_2$, NaH 80%/oil (4.5 mg, 0.112 mmol) was added. Intermediate 6 (60 mg, 0.106 mmol) was added after 30 min, and the reaction mixture was stirred at r.t. for 2 hr. It was then cooled down to r.t. and diluted with water (20 mL). The product was extracted with EtOAc (3×25 mL). The combined organic extracts were washed with sat.aq. NaCl (2×20 mL), and dried over anh. $Na_2SO_4$. The solids were filtered and the solvent evaporated. The crude product was purified by flash chromatography (silica gel, cyclohexane/EtOAc 80%). Intermediate 11 was obtained as a clear oil (28 mg, 0.52 mmol, y=47%).

NMR ($^1$H, CDCl$_3$): δ 7.65 (s, 1H), 7.55 (m, 4H), 7.35 (m, 6H), 7.10 (d, 1H), 6.95 (d, 1H), 3.92 (m, 1H), 3.8 (m, 2H), 3.5-3.3 (m, 2H), 2.21 (m, 1H), 2.44 (s, 3H), 2.10 (s, 3H), 1.61 (m, 1H), 1.10 (s, 9H). MS (m/z): 567[MH]$^+$.

Intermediate 12

4-(4-Chloro-5-hydroxymethyl-2-methyl-6,7-dihydro-5H-pyrido[2,3-d]pyrimidin-8-yl)-3-methyl-benzonitrile To a solution of intermediate 11 (28 mg, 0.05 mmol) in anh. DMF (2.5 mL), at r.t., under $N_2$, Et$_3$N.3HF (44 µL, 0.290 mmol) was added and the reaction mixture was stirred at r.t. for 12 hr. It was diluted with water (20 mL), and the product was extracted with EtOAc (3×25 mL). The combined organic layers were washed with sat. aq. NaCl (2×20 mL) and dried over anh. $Na_2SO_4$. The solids were filtered and the solvent evaporated. The crude product was purified by flash chromatography (silica gel, cHex/EtOAc 6:4). Intermediate 11 was obtained as a clear oil (22 mg, 0.08 mmol, 75%).

NMR ($^1$H, CDCl$_3$): δ 7.61-7.58 (m, 2H), 7.27 (m, 1H), 3.92-3.81 (m, 3H), 3.50-3.35 (m, 2H), 2.4 (m, 1H), 2.26 (s, 3H), 2.19 (s, 3H), 1.8 (m, 1H). MS (m/z): 329[MH]$^+$.

Intermediate 13

4-[1-(1-Ethyl-propyl)-7-methyl-2,2a,3,4-tetrahydro-1H-1,5,6,8-tetraaza-acenaphthylen-5-yl]-3-methyl-benzonitrile To a solution of intermediate 12 (43 mg, 0.131 mmol) in anh. CH$_2$Cl$_2$ (2.5 mL), at 0° C., under $N_2$, MsCl (13 µL, 0.328 mmol) and Et$_3$N (87 µL 0.655 mmol) were added the reaction mixture was stirred at r.t. for 1 hr, and then diluted with water (20 mL). The reaction mixture was extracted with EtOAc. (3×25 mL). The combined organic layers were washed with sat. aq. NaCl (2×20 mL)and dried over anh. $Na_2SO_4$. The solids were filtered and the solvent evaporated. The crude product was dissolved in 3-amino-pentane (143 µL, 1.23 mmol.) and the reaction mixture was heated at 100° C. (screw cap vial, sand bath) for 16 hr. It was then cooled down to r.t. and the reaction mixture was purified by flash chromatography (silica gel, cHex/EtOAc 75:25). Intermediate 13 was obtained as a white solid (23 mg, 0.074 mmol, 50%).

NMR ($^1$H, CDCl$_3$): δ 7.50 (d, 1H), 7.30 (dd, 1H), 7.55 (d, 1H) 3.86 (m, 1H), 3.70-3.23 (t+t, 2H), 3.43 (m, 1H), 3.63 (m, 2H), 2.27 (s, 3H), 2.24 (s, 3H), 2.18 (r, 1H), 1.74 (m, 1H), 1.59-1.45 (m, 4H), 0.99-0.78 (t+t 6H). MS (m/z): 362[MH]$^+$.

Intermediate 14

3-Methyl-4-[7-methyl-1-(1-propyl-butyl)-2,2a,3,4-tetrahydro-1H-1,5,6,8-tetraaza-acenaphthylen-5-yl]-benzonitrile To a solution of intermediate 12 (14 mg, 0.043 mmol) in anh. CH$_2$Cl$_2$ (1.5 mL), at 0° C., under $N_2$, MsCl (4µL, 0.109 mmol) and Et$_3$N (28 µL 0.216 mmol) were added the reaction mixture was stirred at r.t. for 1 hr, and then diluted with water (20 mL). The product was extracted with EtOAc (3×25 mL). The combined organic layers were washed with sat. aq. NaCl (2×20 mL) and dried over anh. $Na_2SO_4$. The solids were filtered and the solvent evaporated. The crude product was dissolved in 4-heptylamine (50 µL, 0.349 mmol) and the reaction mixture was heated at 100° C. (screw cap vial, sand bath) for 16 hr. It was then cooled down to r.t. and the reaction mixture was purified by flash chromatography (sililca gel, cHex/EtOAc 75:25). Intermediate 14 was obtained as a white solid (5.0 mg, 0.020 mmol, 40%).

NMR ($^1$H, CDCl$_3$): δ 7.73 (s, 1H), 7.65 (dd, 1H), 7.41 (d, 1H) 3.95 (m, 1H), 3.78-3.6 (m, 2H), 3.5-3.24 (t, 2H), 2.27 (m, 1H), 2.18 (s, 3H), 2.10 (s, 3H), 1.65 (m, 1H), 1.55-1.40 (m, 4H), 1.38-1.10 (m, 4H), 0.95-0.88 (t+t, 6H). MS (m/z): 389 [MH]$^+$.

Intermediate 15

4-[5-(tert-Butyl-diphenyl-silanyloxymethyl)-4-chloro-2-methyl-6,7-dihydro-5H-pyrido[2,3-d]pyrimidin-8-yl]-3-chloro-benzonitrile To a solution of 4-amino-3-chlorobenzonitrile (86 mg, 0.566 mmol) in DMF (3.5 mL), at 0° C., under $N_2$, NaH 80%/oil (17 mg, 0.566 mmol) was added. Intermediate 6 (308 mg, 0.546 mmol) was added after 30 min, and the reaction mixture was stirred at r.t. for 2 hr. It was then cooled down to r.t. and diluted with water (30 mL). The product was extracted with EtOAc (3×45 mL). The combined organic extracts were washed with sat.aq. NaCl (2×20 µL), and dried over anh. $Na_2SO_4$. The solids were filtered and the solvent evaporated. The crude product was purified by flash chromatography (silica gel, cHex/EtOAc 8:2). Intermediate 15 was obtained as a clear oil (110 mg, 0.184 mmol, 35%).

NMR ($^1$H, CDCl$_3$): δ 7.65 (s, 1H), 7.55 (m, 4H), 7.35 (m, 6H), 7.10(d, 1H), 6.95 (d, 1H), 3.92 (m, 1H), 3.8 (m, 2H), 3.5-3.3 (m, 2H), 2.21 (m, 1H), 2.10 (s, 3H), 1.61 (m, 1H), 1.10 (s, 9H). MS (m/z): 587[MH]$^+$.

Intermediate 16

3-Chloro-4-(4-chloro-5-hydroxymethyl-2-methyl-6,7-dihydro-5H-pyrido[2,3-d]pyrimidin-8-yl)benzonitrile To a solution of intermediate 15 (110 mg, 0.19 mmol) in anh. DMF (2.5 mL), at r.t., under $N_2$, Et$_3$N.3HF (260 µL, 1.91 mmol) was added and the reaction mixture was stirred at r.t. for 12 hr. It was diluted with water (20 mL), and the product was extracted with EtOAc (3×20 mL). The combined organic layers were washed with sat aq. NaCl (2×20 mL) and dried over anh. $Na_2SO_4$. The solids were filtered and the solvent evaporated. The crude product was purified by flash chromatography (silica gel, cHex/EtOAc 6:4). Intermediate 16 was obtained as clear oil (53 mg, 0.15 mmol, 81%).

NMR ($^1$H, CDCl$_3$): δ 7.95-8.8(m, 2H), 7.3(d, 1H), 3.9(m, 1H), 3.(m, 2H), 3.5-3.3 (m, 2H), 2.2 (m, 1H), 2.15 (s, 3H), 1.8 (m, 1H). MS (m/z): 349[MH]$^+$.

Intermediate 17

3-Chloro-4-[7-methyl-1-(1-propyl-butyl)-2,2a,3,4-tetrahydro-1H-1,5,6,8-tetraaza-acenaphthylen-5-yl]-benzonitrile To a solution of intermediate 16 (52 mg, 0.149 mmol) in anh. CH$_2$Cl$_2$ (1.5 mL), at 0° C., under N$_2$, MsCl (16 μL, 0.373 mmol) and Et$_3$N (90 μL 0.745 mmol) were added. The reaction mixture was stirred at r.t. for 1 hr, and then diluted with water (20 mL). The product was extracted with EtOAc (3×25 mL). The combined organic layers were washed with sat. aq. NaCl (2×20 mL) and dried over anh. Na$_2$SO$_4$. The solids were filtered and the solvent evaporated. The crude product was dissolved in 4-heptylamine (188 μL, 1.49 mmol.) and the reaction mixture was heated at 100° C. (screw cap vial, sand bath) for 16 hr. It was then cooled down to r.t. and the reaction mixture was purified by flash chromatography (slilca gel, cHex/EtOAc 8:2). Intermediate 17 was obtained as a white solid (36.0 mg, 0.084 mmol, 60%).

NMR ($^1$H, CDCl$_3$): δ 7.74 (d, 1H), 7.56 (dd, 1H), 7.49 (d, 1H) 4.05 (m, 1H), 3.78-3.6 (m, 2H), 3.5-3.24 (t, 2H), 2.27 (s, 3H), 2.18 (m, 1H), 1.55-1.40 (m, 4H), 1.38-1.10 (m, 4H), 0.95-0.88 (t+t 6H). MS (m/z): 410[MH]$^+$.

Intermediate 18

3-Chloro-4-[1-(1-ethyl-propyl)-7-methyl-2,2a,3,4-tetrahydro-1H-1,5,6,8-tetraaza-acenaphthylen-5-yl]-benzonitrile To a solution of intermediate 16 (35 mg, 0.112 mmol) in anh. CH2Cl$_2$ (1.5 mL), at 0° C., under N$_2$, MsCl (12 μl, 0.277 mmol) and Et$_3$N (68 μl 0.560 mmol) were added and the reaction mixture was stirred at r.t. for 1 hr, and then diluted with water (20 mL). The product was extracted with EtOAc (3×25 mL). The combined organic layers were washed with sat. aq. NaCl (2×20 mL) and dried over anh. Na$_2$SO$_4$. The solids were filtered and the solvent evaporated. The crude product was dissolved in 3-amino-pentane (158 μL, 1.12 mmol.) and the reaction mixture was heated at 100° C. (screw cap vial, sand bath) for 16 hr. It was then cooled down to r.t. and the reaction mixture was purified by flash chromatography (slilca gel, cHex/EtOAc 75:25). Intermediate 18 was obtained as a white solid (18.0 mg, 0.084 mmol, 53%).

NMR ($^1$H, CDCl$_3$): δ 7.74 (d, 1H), 7.55 (dd, 1H), 7.50 (d, 1H) 3.95 (mn, 1H), 3.78-3.65 (m, 2H), 3.45 (m, 1H), 3.69-3.23 (t+t, 2H), 2.28 (s, 3H), 2.18 (m, 1H), 1.55-1.46 (m, 4H), 0.97-0.78 (t+t, 6H). MS (m/z): 382[MH]$^+$.

Intermediate 19

5-(2,4-Bis-trifluoromethyl-phenyl)-1-(1-ethyl-propyl)-7-methyl-1,2,2a,3,4,5-hexahydro-1,5,6,8-tetraaza-acenaphthylene To a solution of intermediate 8 (45 mg, 0.106 mmol) in anh. CH$_2$Cl$_2$ (2.5 mL), at 0° C., under N$_2$, MsCl (10 μL, 0.265 mmol) and Et$_3$N (70 μL 0.530 mmol) were added and the reaction mixture was stirred at r.t. for 1 hr, and then diluted with water (20 mL). The product was extracted with EtOAc (3×25 mL). The combined organic layers were washed with sat. aq. NaCl (2×20 mL) and dried over anh Na$_2$SO$_4$. The solids were filtered and the solvent evaporated The crude product was dissolved in 3-amino-pentane (184 μL, 0.992 mmol.) and the reaction mixture was heated at 100° C. (screw cap vial, sand bath) for 16 hr. It was then cooled down to r.t. and the reaction mixture was purified by flash chromatography (silica gel, cHex/EtOAc 75:25). Intermediate 19 was obtained as a white solid (28.0 mg, 0.064 mmol, 60%).

NMR ($^1$H, CDCl$_3$): δ 7.98 (d, 1H), 7.83 (dd, 1H), 7.49 (d, 1H) 3.87 (m, 1H), 3.70-3.23 (t+t, 2H), 3.44 (m, 1H), 3.63 (m, 2H), 2.23 (s, 3H), 2.18 (m, 1H), 1.55-1.47 (m, 4H), 0.99-0.88 (t+t, 6H). MS (m/z): 458[MH]$^+$.

Example 5-1-1

7-Methyl-1-(1-propyl-butyl)-5-[4-(1,1,2-trifluoro-ethyl-2-trifluoromethylphenyl]-1,2,2a,3,4,5-exahydro-1,5,6,8-tetraaza-acenaphtylene To a solution of intermediate 10 (21 mg, 0.043 mmol) in anh. CH$_2$Cl$_2$ (1.0 mL), DDQ (9.7 mg 1 eq) was added. The reaction mixture was stirred at r.t. for 3.5 hr. The solvent was evaporated and the crude product was purified by flash chromatography (silica gel, cHex/EtOAc 9:1). Example 5-1-1 was obtained as a clear oil (14 mg, 0.028 mmol, 67%).

Example 5-1-2

3-Methyl-4-[7-methyl-1-(1-propyl-butyl-3,4-dihydro-1,H-1,5,6,8-tetraaza-acenaphthylen-5-yl]-benzonitrile To a solution of intermediate 14 (15 mg, 0.038 mmol) in CH$_2$Cl$_2$ (1.5 mL), DDQ (9.6 mg 0.042 mmol) was added. The reaction mixture was stirred at r.t. for 3 hr. The solvent was evaporated and the crude product was purified by flash chromatography (silica gel, cyclohexane/EtOAc 7:3) Example 5-1-2 was obtained as a white solid (8 mg, 0.021 mmol, 56%).

Example 5-1-3

4-[1-(1-Ethyl-propyl)-7-methyl-3,4-dihydro-1H-1,5,6,8-tetraaza-acenaphthylen-5-yl]-3-methyl-benzonitrile To a solution of intermediate 13 (18 mg, 0.049 mmol) in CH$_2$Cl$_2$ (1.5 mL), DDQ (14.5 mg 0.064 mmol) was added. The reaction mixture was stirred at r.t. for 3 hr. The solvent was evaporated and the crude product was purified by flash chromatography (slilca gel, cHex/EtOAc 7:3). Example 5-1-3 was obtained as a white solid (10 mg, 0.029 mmol, 60%).

Example 5-1-4

3-Chloro-4-[7-methyl-1-(1-propyl-butyl)-3,4-dihy-dro-1H-1,5,6,8-tetraaza-acenaphthylen-5-yl]-benzonitrile To a solution of intermediate 17 (15 mg, 0.04 mmol) in anh. CH$_2$Cl$_2$ (1.0 mL), DDQ (14.5 mg 0.064 mmol) was added. The reaction mixture was stirred at r.t. for 3 hr. The solvent was evaporated and the crude product was purified by flash chromatography (silica gel, cHex/EtOAc 7:3). Example 5-1-4 was obtained as a white solid (8.1 mg, 0.02 mmol, 56%).

Example 5-1-5

3-Chloro-4-[1-(1-ethyl-propyl)-7-methyl-3,4-dihydro-1H-1,5,6,8-tetraaza-acenaphthylen-5-yl]-benzonitrile To a solution of intermediate 18 (12 mg, 0.032 mmol) in anh. CH$_2$Cl$_2$ (1.0 mL), DDQ (10.5 mg 0.042 mmol) was added. The reaction mixture was stirred at r.t. for 3 hr. The solvent was evaporated and the crude product was purified by flash chromatography (slilca gel, cHex/EtOAc 7:3). Example 5-1-5 was obtained as a white solid (8.0 mg, 0.02 mmol, 60%).

Example 5-1-6

5-(2,4-Bis-trifluoromethyl-phenyl-1-(1-ethyl-propyl)-7-methyl-1,3,4,5-tetrahydro-1,5,6,8-tetraaza-acenaphthylene To a solution of intermediate 19 (20 mg, 0.044 mmol) in anh. CH$_2$Cl$_2$ (1.5 mL), DDQ (12.5 mg 0.053 mmol) was added. The reaction mixture was stirred at r.t. for 3 h The solvent was evaporated and the crude product was purified by flash chromatography (slilca gel, cHex/EtOAc 7:3). Example 5-1-6 was obtained as a white solid (11 mg, 0.024 mmol, 60%).

All the analytical data are set forth in the following Table 1.

TABLE 1

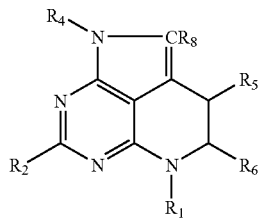

(XIa)

| Cpd. No. | R$_1$ | R$_2$ | R$_4$" | R$_8$, R$_5$, R$_6$" | Analitycal Data |
|---|---|---|---|---|---|
| 5-1-1 | 2,4-bistrifluoromethylphenyl | CH$_3$ | (3-pentyl) | H | NMR($^1$H, CDCl$_3$): δ 8.05(s, 1H), 7.89(d, 1H), 7.65(d, 1H), 6.58(s, 1H), 4.62(m, 1H), 3.78(m, 2H), 3.40-3.00(m, 2H), 2.49(s, 3H), 1.80(m, 8H), 1.30-1.10, 0.88 (m, t, 8H). MS(m/z): 485[MH]$^+$. |
| 5-1-2 | 2-methyl-4-cyanophenyl | CH$_3$ | (4-heptyl) | H | NMR($^1$H, CDCl$_3$): δ 7.59(d, 1H), 7.56(d, 1H), 7.40(dd, 1H), 6.59 (s, 1H), 4.65(m, 1H), 3.84(t, 2H), 3.14(t, 2H), 2.52(s, 3H), 2.28(s, 3H), 1.79(m, 4H), 1.25(m, 4H), 0.84(t, 6H). MS(m/z): 388[MH]$^+$. |
| 5-1-3 | 2-methyl-4-cyanophenyl | CH$_3$ | (3-pentyl) | H | NMR($^1$H, CDCl$_3$): δ 7.70(d, 1H), 7.56(d, 1H), 7.43(dd, 1H), 6.60 (s, 1H), 4.54(m, 1H), 3.91(t, 2H), 3.16(t, 2H), 2.53(s, 3H), 2.29(s, 3H), 1.79(m, 4H), 0.84 (t, 6H). MS(m/z): 360[MH]$^+$. |
| 5-1-4 | 2-chloro-4-cyanophenyl | CH$_3$ | (4-heptyl) | H | NMR($^1$H, CDCl$_3$): δ 7.80(d, 1H), 7.73(d, 1H), 7.63(dd, 1H), 6.62 (s, 1H), 4.51(m, 1H), 3.92(t, 2H), 3.18(t, 2H), 2.55(s, 3H), 1.79(m, 4H), 1.25(m, 4H), 0.88 (t, 6H). MS(m/z): 408[MH]$^+$. |

TABLE 1-continued

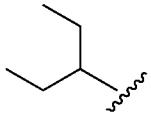

(XIa)

| Cpd. No. | R$_1$ | R$_2$ | R$_4$" | R$_8$, R$_5$, R$_6$" | Analitycal Data |
|---|---|---|---|---|---|
| 5-1-5 | 2-chloro-4-cyanophenyl | CH$_3$ | | H | NMR($^1$H, CDCl$_3$): δ 7.80(d, 1H), 7.73(d, 1H), 7.63(dd, 1H), 6.62 (s, 1H), 4.51(m, 1H), 3.92(t, 2H), 3.18(t, 2H), 2.55(s, 3H), 1.79(m, 4H), 0.88(t, 6H). MS(m/z): 380[MH]$^+$. |
| 5-1-6 | 2,4-bistrifluoro-methylphenyl | CH$_3$ | | H | NMR($^1$H, CDCl$_3$): δ 9.92(d, 1H), 8.03(d, 1H), 7.69(dd, 1H), 6.62 (s, 1H), 4.58(m, 1H), 3.81(t, 2H), 3.18(t, 2H), 2.51(s, 3H), 1.92(m, 4H), 0.83(t, 6H). MS(m/z): 457[MH]$^+$. |

Example 6

Synthesis of Representative Compounds of Structure (XIb)

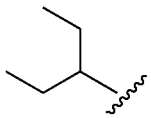

(XIb)

Intermediate 20

4-Chloro-3-(2-methoxy-vinyl)-6-methyl-1-(1-propyl-butyl)-1H-pyrrolo[3,2-c]pyridine To a solution of (methoxymethyl)-triphenylphosphonium chloride (70 mg, 3 eq) in anh. THF (1 mL), at 0° C., under N$_2$, BuLi 1.6M in THF (128 µL, 3 eq) was added dropwise. The resulting red reaction mixture was stirred at 0° C. for 10 min and further 20 min at r.t. Then the reaction mixture was cooled at 0° C. and a solution of 4-chloro-6-methyl-1-(1-propyl-butyl)-1H-pyrrolo[3,2]pyridine-3-carbaldehyde (prepared following procedures reported in J. Heterocyclic Chem.; 1996, 33, 303; J. Heterocyclic Chem.; 1992, 29, 359; Heterocycles; 2000, 53, 11, 2415; Tetrahedron; 1985, 41, 10, 1945. analytical data: NMR ($^1$H, DMSO): δ 8.49 (s, 1H), 7.70 (s, 1H), 10.4 (s, 1H), 2.53 (s, 3H), 4.57 (m, 1H), 1.92/1.79 (m/m 4H), 1.70/0.90 (m/m 4H), 0.77 (t, 6H); MS (m/z): 293 [MH]$^+$) (20 mg, 0.068 mmol) in anh. THF (1 mL) was added dropwise.

The reaction mixture was stirred at r.t. for 1 hr. Then water (3 mL) was added and the product was extracted with EtOAc (3×5 mL). The combined organic layers were washed with sat.aq. NaCl (1×5 mL) and dried over anh. Na$_2$SO$_4$. The solids were filtered and the solvent evaporated to give a crude product, which was purified by flash chromatography (silica gel, cHex/EtOAc 95:05). Intermediate 20 was obtained as a yellow oil (15 mg, 0.046 mmol, 70%)

NMR ($^1$H, CDCl$_3$): δ (trans) 6.98 (s, 1H), 2.59 (s, 3H), 6.69, (s, 1H), 6.81 (d, 1H), 6.40 (d, 1H), 4.21 (m, 1H), 1.82 (m, 4H), 1.53 (m, 4H), 0.85 (dt, 6H), 3.83 (s, 3H0; (cis) 6.94 (s, 1H), 2.59 (s, 3H), 7.62, (s, 1H), 4.21 (m, 1H), 1.82 (m, 4H), 1.53 (m, 4H), 0.85 (dt, 6H), 6.19 (d, 1H), 6.30 (d, 1H), 3.72 (s, 3H), MS (m/z): 321 [MH]$^+$.

Intermediate 21

[4-Chloro-6-methyl-1-(1-propyl-butyl)-1H-pyrrolo[3,2-c]pyridin-3-yl]-acetaldehyde To a solution of intermediate 20 (85 mg, 0.26 mmol) in anh. THF (2 mL) at 0° C., under N$_2$, HCl 2N (2 mL) was added dropwise. The resulting yellow reaction mixture was stirred at 70° C. for 1.5 hr. Then sat.aq. NaHCO$_3$ (1 mL) was added and the product was extracted with EtOAc (3×5 mL). The combined organic layers were washed with sataq. NaCl (1×5 mL) and dried over anh. Na$_2$SO$_4$. The solids were filtered and the solvent evaporated to give a crude product, which was purified by flash chromatography (silica gel, cHex/EtOAc 8:2). Intermediate 21 was obtained as a yellow oil (55 mg, 0.179 mmol, 70%)

NMR ($^1$H, CDCl$_3$): δ 9.85 (s, 1H), 7.07 (s, 1H), 7.01, (s, 1H), 4.21 (m, 1H), 4.04 (s, 2H), 2.60 (s, 3H), 1.82 (m, 4H), 1.16 (m, 4H), 0.85 (dt, 6H). MS (m/z): 307 [MH]$^+$.

Intermediate 22

[4-Chloro-6-methyl-1-(1-propyl-butyl)1H-pyrrolo[3,2-c]pyridin-3-yl]ethanol

To a solution of intermediate 21 (53 mg, 0.173 mmol) in anh. MeOH (4 mL) at 0° C., under N$_2$, NaBH$_4$ (13.1 mg, 2 eq) was added. The reaction mixture was stirred at 0° C. for 1 hr. Then water (1 mL) was added and the product was extracted with EtOAc (3×5 mL). The combined organic layers were washed with sat.aq. NaCl (1×5 mL) and dried over anh. Na$_2$SO$_4$. The solids were filtered and the solvent evaporated to give a crude product, which was purified by flash chromatography (silica gel, cHex/EtOAc 7:3). Intermediate 22 was obtained as a yellow oil (49.8 mg, 0.161 mmol, 93%)

NMR ($^1$H, DMSO): δ 7.37 (s, 1H), 7.33, (s, 1H), 4.63 (t, 1H), 3.64 (t, 2H), 3.01 (t, 2H), 2.44 (s, 3H), 1.77 (m, 4H), 0.89-1.79 (m, 4H), 0.77 (t, 6H). MS (m/z): 309 [MH]$^+$.

Intermediate 23

3-[2-(tert-Butyl-dimethyl-silanyloxy)-ethyl]-4-chloro-6-methyl-1-(1-propyl-butyl)-1H-pyrrolo[3,2-c]pyridine To a solution of intermediate 22 (49.8 mg, 0.173 mmol) in anh. DMF (2 mL) at 0° C., under N$_2$, imidazole (110 mg, 10 eq), TBSCl (67 mg, 2.8 eq), DMAP (2 mg, 0.1 eq) were added. The reaction mixture was stirred at r.t. overnight. Then water (1 mL) was added and the product was extracted with Et$_2$O (3×5 mL). The combined organic layers were washed with sataq. NaCl (1×5 mL) and dried over anh. Na$_2$SO$_4$. The solids were filtered and the solvent evaporated to give a crude product, which was purified by flash chromatography (silica gel, cHex/EtOAc 9:1). Intermediate 23 was obtained as a yellow oil (65 mg, 0.154 mmol, 95%).

NMR ($^1$H, DMSO): δ 6.95 (s/s, 1/1H), 4.17 (m, 1H), 3.91 (t, 2H), 3.16 (t, 2H), 2.58 (s, 3H), 1.80 (m, 4H), 1.14-1.05 (m/m, 4H), 0.88 (s, 9H), 0.85 (t, 6H), 0.00 (s, 6H). MS (m/z): 423 [MH]$^+$.

Intermediate 24

(2,4-Bis-trifuoromethyl-phenyl)-[3-[2-(tert-Butyl-dimethyl-silanyloxy)-ethyl]-6-methyl-1-(1-propyl-butyl)-1H-pyrrolo[3,2-c]pyridin-4-yl]-amine To a mixture of tris(dibenzylideneacetone)palladium(0) (3.7 mg, 0.1 eq), 2-(dicyclohexylphosphino)-2'-methylbiphenyl (4.4 mg, 0.3 eq), K$_3$PO$_4$ (23 mg, 2.8 eq) a solution of intermediate 23 (17 mg, 0.04 mmol) and 2,4-bis(trifluoromethyl)anilin (18 mg, 2 eq) in anh. DME (1 mL) at r.t., under N$_2$, was added (crimp cap microwave vial). The reaction mixture was irradiated in CEM Focused Microwave Synthesis System (Model Discovery), at 100° C., 150 W, 60 Psi for 20 min (cooling on). Then water (1 mL) was added and the product was extracted with Et$_2$O (3×5 mL). The combined organic layers were washed with sataq. NaCl (1×5 mL) and dried over anh. Na$_2$SO$_4$. The solids were filtered and the solvent evaporated to give a crude product, which was purified by flash chromatography (silica gel, cHex/EtOAc 95:05). Intermediate 24 was obtained as a yellow oil (21.5 mg, 0.035 mmol, 88%).

NMR ($^1$H, DMSO): δ 7.83 (d, 1H), 7.79 (dd, 1H), 8.16 (d, 1H), 8.23 (s, 1), 7.22 (s, 1H), 7.16 (s, 1H), 2.43 (s, 3H), 4.35 (m, 1H), 3.77 (t, 2H), 2.94 (t, 2H), 1.8 (m, 4H), 1.15, 0.95(m/m, 4H), 0.79 (t; 6H), 0.68 (s, 9H), −0.31 (s, 6H). MS (m/z): 616 [MH]$^+$.

Intermediate 25

2-[4-(2,4-Bis-trifluoromethyl-phenyl)-6-methyl-1-(1-propyl-butyl)-1H-pyrrolo[3,2-c]pyridin-3-yl]-ethanol To a solution of intermediate 24 (60 mg, 0.097 mmol) in dry D (5 mL) at r.t. Et$_3$N.3HF (133.6 µL, 8.4 eq) was added. The reaction mixture was stirred at r.t. overnight. Then water (2 mL) was added and the product was extracted with EtOAc (3×5 mL). The combined organic layers were washed with sat.aq. NaCl (1×5 mL) and dried over anh. Na$_2$SO$_4$. The solids were filtered and the solvent evaporated to give a crude product, which was purified by flash chromatography (silica gel, cHex/EtOAc 9:1). Intermediate 25 was obtained as a white solid (24.4 mg, 0.048 mmol, 50%).

NMR ($^1$H, DMSO): δ 9.01 (sa, 1H), 8.07 (d, 1H), 7.81 (s, 1H), 7.76 (dd, 1H), 7.19 (s, 1H), 7.10 (s, 1H), 5.19 (sa, 1H), 4.35 (m, 1H), 3.63 (m, 2H), 2.88 (m, 2H), 2.38 (s, 3H), 1.85-1.65 (m, 4H), 1.20,0.90 (m, 4H), 0.80 (m, 6H). MS (m/z): 502 [MH]$^+$.

Example 6-1-1

5-(2,4-Bis-trifluoromethyl-phenyl)-7-methyl-1-(1-propyl-butyl)-1,3,4,5-tetrahydro-1,5,6-triaza-acenaphthylene To a solution of intermediate 25 (23.4 mg, 0.04 mmol) in dry CH$_2$Cl$_2$ (2 mL) at r.t. Et$_3$N (13.5 µL, 2 eq) and MsCl (6.16 µL, 2 eq) were added. The reaction mixture was stirred at r.t. for 2 hr. Then water (2 mL) was added and the product was extracted with CH$_2$Cl$_2$ (3×5 mL). The combined organic layers were washed with sat.aq. NaCl (1×5 mL) and dried over anh. Na$_2$SO$_4$. The solids were filtered and the solvent evaporated to give a crude product, which was purified by flash chromatography (silica gel, cHex/EtOAc 9:1). Example 6-1-1 was obtained as a yellow oil (6 mg, 0.012 mmol, 31%).

All the analytical data are set forth in the following Table 1.

TABLE 1

(XIb)

| Cpd. No. | R$_1$ | R$_2$ | R$_4$" | R$_8$, R$_3$, R$_5$, R$_6$" | Analitycal Data |
|---|---|---|---|---|---|
| 6-1-1 | 2,4-bistrifluoro-methylphenyl | CH$_3$ | (4-heptyl group) | H | NMR($^1$H, DMSO): δ 8.08(dd, 1H), 8.03(s, 1H), 7.81(d, 1H), 6.87(s, 1H), 6.61(s, 1H), 4.19 (m, 1H), 3.72(t, 2H), 3.02(t, 2H), 2.19(s, 3H), 1.80-1.70(m, 4H), 1.30-1.10(m, 4H), 0.79(m, 6H). MS(m/z): 483 [MH]$^+$. |

Example 7

CRF Receptor Binding Activity

The compounds of this invention may be evaluated for binding activity to the CRF-receptor by a standard radioligand binding assay as generally described by DeSouza et al. (*J. Neurosci.* 7:88-100, 1987). By utilizing various radiolabeled CRF ligands, the assay may be used to evaluate the binding activity of the compounds of the present invention with any CRF receptor subtype. Briefly, the binding assay involves the displacement of a radiolabeled CRF ligand from the CRF receptor.

More specifically, the binding assay is performed in 1.5 mL Eppendorf tubes using approximately 1×10$^6$ cells per tube stably transfected with human CRF receptors. Each tube receives about 0.1 mL of assay buffer (eg., Dulbecco's phosphate buffered saline, 10 mM magnesium chloride, 20 μM bacitracin) with or without unlabeled sauvagine, urotensin I or CRF (final concentration, 1 μM) to determine nonspecific binding, 0.1 ml of [$^{125}$I] tyrosine—ovine CRF (final concentration ~200 pM or approximately the K$_D$ as determined by Scatchard analysis) and 0.1 mL of a membrane suspension of cells containing the CRF receptor. The mixture is incubated for 2 hours at 22° C. followed by the separation of the bound and free radioligand by centrifugation. Following two washes of the pellets, the tubes are cut just above the pellet and monitored in a gamma counter for radioactivity at approximately 80% efficiency. All radioligand binding data may be analyzed using the nonlinear least-square curve-fitting program LIGAND of Munson and Rodbard (*Anal. Biochem.* 107:220, 1990).

Example 8

CRF-Stimulated Adenylate Cyclase Activity

The compounds of the present invention may also be evaluated by various functional testing. For example, the compounds of the present invention may be screened for CRF-stimulated adenylate cyclase activity. An assay for the determination of CRF-stimulated adenylate cyclase activity may be performed as generally described by Battaglia et al. (*Synapse* 1:572, 1987), with modifications to adapt the assay to whole cell preparations. More specifically, the standard assay mixture may contain the following in a final volume of 0.5 mL: 2 mM L-glutamine, 20 mM HEPES, and 1 mM IMBX in DMEM buffer. In stimulation studies, whole cells with the transfected CRF receptors are plated in 24-well plates and incubated for 1 h at 37° C. with various concentrations of CRF-related and unrelated peptides in order to establish the pharmacological rank-order profile of the particular receptor subtype. Following the incubation, the media is aspirated, the wells rinsed once gently with fresh media, and the media aspirated. To determine the amount of intracellular cAMP, 300 μl of a solution of 95% ethanol and 20 mM aqueous hydrochloric acid is added to each well and the resulting suspensions are incubated at −20° C. for 16 to 18 hours. The solution is removed into 1.5 mL Eppendorf tubes and the wells washed with an additional 200 μl of ethanol/aqueous hydrochloric acid and pooled with the first fraction. The samples are lyophilized and then resuspended with 500 μl sodium acetate buffer. The measurement of cAMP in the samples is performed using a single antibody kit from Biomedical Technologies Inc. (Stoughton, Mass.). For the functional assessment of the compounds, a single concentration of CRF or related peptides causing 80% stimulation of cAMP production is incubated along with various concentrations of competing compounds ($10^{-12}$ to $10^{-6}$ M).

It will be appreciated that, although specific embodiments of the invention have been described herein for purposes of illustration, various modifications may be made without departing from the spirit and scope of the invention.

Accordingly, the invention is not limited except as by the appended claims.

What is claimed is:

1. A compound having the following structure:

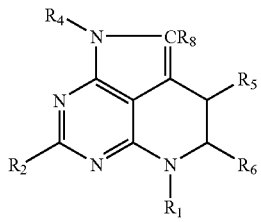

(XIa)

wherein
- $R_1$ is alkyl, substituted alkyl, aryl, substituted aryl, heteroaryl, or substituted heteroaryl;
- $R_2$ is hydrogen, alkyl, substituted alkyl, alkoxy, thioalkyl, halo, cyano, or haloalkyl;
- $R_4$ is hydrogen, alkyl, substituted alkyl or $C(O)R_1$;
- $R_5$ is hydrogen, halogen, alkyl, substituted alkyl, aryl, substituted aryl, heteroaryl, substituted heteroaryl, alkoxy, thioalkyl, $C(O)R_1$, $NR_{10}R_{11}$ or cyano;
- $R_6$ is hydrogen, halogen, alkyl, substituted alkyl, aryl, substituted aryl, heteroaryl, substituted heteroaryl, alkoxy, thioalkyl, $C(O)$alkyl, $NR_{10}R_{11}$ or cyano;
- $R_8$ is hydrogen, halogen, alkyl, substituted alkyl, aryl, substituted aryl, heteroaryl, substituted heteroaryl, alkoxy, thioalkyl, $C(O)$alkyl, $NR_{10}R_{11}$ or cyano; and
- $R_{10}$, $R_{11}$ are the same or different and are independently hydrogen, alkyl, substituted alkyl, aryl, substituted aryl, heteroaryl, or substituted heteroaryl; or a pharmaceutically acceptable salt thereof.

2. A compound having the following structure:

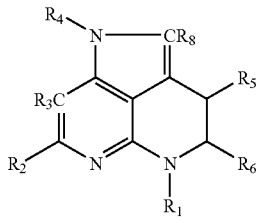

(XIb)

wherein
- $R_1$ is alkyl, substituted alkyl, aryl, substituted aryl, heteroaryl, or substituted heteroaryl;
- $R_2$ is hydrogen, alkyl, substituted alkyl, alkoxy, thioalkyl, halo, cyano, or haloalkyl;
- $R_3$ is hydrogen, alkyl, substituted alkyl, halo or haloalkyl;
- $R_4$ is hydrogen, alkyl, substituted alkyl, $C(O)R_1$, aryl, substituted aryl, heterocycle or substituted heterocycle;
- $R_5$ is hydrogen, halogen, alkyl, substituted alkyl, aryl, substituted aryl, heteroaryl, substituted heteroaryl, alkoxy, thioalkyl, $C(O)R_1$, $NR_{10}R_{11}$ or cyano;
- $R_6$ is hydrogen, halogen, alkyl, substituted alkyl, aryl, substituted aryl, heteroaryl, substituted heteroaryl, alkoxy, thioalkyl, $C(O)R_1$, $NR_{10}R_{11}$ or cyano;
- $R_8$ is hydrogen, halogen, alkyl, substituted alkyl, aryl, substituted aryl, heteroaryl, substituted heteroaryl, alkoxy, thioalkyl, $C(O)$alkyl, $NR_{10}R_{11}$ or cyano; and
- $R_{10}$, $R_{11}$ are the same or different and are independently hydrogen, alkyl, substituted alkyl, aryl, substituted aryl, heteroaryl, or substituted heteroaryl; or a pharmaceutically acceptable salt thereof.

3. A compound selected from the group consisting of:
7-methyl-1-(1-propyl-butyl)-5-[4-(1,1,2-trifluoro-ethyl)-2-trifluoromethylphenyl]-1,2,2a,3,4,5-hexahydro-1,5,6,8-tetraaza-acenaphthylene;
3-methyl-4-[7-methyl-1-(1-propyl-butyl)-3,4-dihydro-1H-1,5,6,8-tetraaza-acenaphthylen-5-yl]-benzonitrile;
4-[1-(1-ethyl-propyl)-7-methyl-3,4-dihydro-1H-1,5,6,8-tetraaza-acenaphthylen-5-yl]-3-methyl-benzonitrile;
3-chloro-4-[7-methyl-1-(1-propyl-butyl)-3,4-dihydro-1H-1,5,6,8-tetraaza-acenaphthylen-5-yl]-benzonitrile;
3-chloro-4-[1-(1-ethyl-propyl)-7-methyl-3,4-dihydro-1H-1,5,6,8-tetraaza-acenaphthylen-5-yl]-benzonitrile;
5-(2,4-bis-trifluoromethyl-phenyl)-1-(1-ethyl-propyl)-7-methyl-1,3,4,5-tetrahydro-1,5,6,8-tetraaza-acenaphthylene; and
8-[2,4-bis(trifluoromethyl)phenyl]-4,6,7,8-tetrahydro-2-methyl-4-(1-propylbutyl)-pyrrolo[2,3,4-de]-1,8-naphthyridine; or a pharmaceutically acceptable salt thereof.

4. A composition comprising a compound of claim 1, or a pharmaceutically acceptable salt thereof, in combination with a pharmaceutically acceptable carrier or diluent.

5. A composition comprising a compound of claim 2, or a pharmaceutically acceptable salt thereof, in combination with a pharmaceutically acceptable carrier or diluent.

* * * * *